United States Patent [19]

Ando et al.

[11] Patent Number: 5,395,958

[45] Date of Patent: Mar. 7, 1995

[54] CYCLOPROPENE DERIVATIVES

[75] Inventors: Ryoichi Ando, Kanagawa; Yasuhiro Morinaka, Ibaraki; Eiichi Nakamura, Tokyo, all of Japan

[73] Assignee: Mitsubishi Kasei Corporation, Tokyo, Japan

[21] Appl. No.: 126,646

[22] Filed: Sep. 27, 1993

[30] Foreign Application Priority Data

Sep. 30, 1992 [JP] Japan ................................. 4-262473
Sep. 30, 1992 [JP] Japan ................................. 4-262474
Sep. 30, 1992 [JP] Japan ................................. 4-262475

[51] Int. Cl.$^6$ .................. C07C 69/74; C07C 215/00; C07C 233/00; C07D 327/00
[52] U.S. Cl. .................................. 560/124; 564/443; 564/339; 564/157; 564/155; 564/152; 564/453; 549/4; 549/77; 549/495

[58] Field of Search ............... 564/443, 453, 152, 155, 564/157; 560/124; 514/18, 19; 549/4, 77, 495; 562/506

[56] References Cited

U.S. PATENT DOCUMENTS 4,474,800 10/1984 Tamai et al. ..................... 424/278
4,714,777 12/1987 Dowd et al. ..................... 562/506
5,081,284 1/1992 Higuchi et al. ................... 560/159
5,158,936 10/1992 Krantz et al. ..................... 514/19

Primary Examiner—Richard L. Raymond
Assistant Examiner—Deborah Lambkin
Attorney, Agent, or Firm—Wenderoth, Lind & Ponack

[57] ABSTRACT

The cyclopropene derivatives of the present invention are useful as the intermediates for producing cyclopropenone derivatives exhibiting strong inhibition activity of thiol protease such as calpain, papain, cathepsin B, cathepsin H, cathepsin L and the like.

3 Claims, No Drawings

CYCLOPROPENE DERIVATIVES

FIELD OF THE INVENTION

The present invention relates to novel cyclopropene derivatives, and more specifically, the present invention relates to novel cyclopropene derivatives useful as intermediates for the production of cyclopropenone derivatives having strong inhibitory activity against thiol protease such as calpain, papain, cathepsin B, cathepsin H, cathepsin L and the like, or the salts thereof.

BACKGROUND OF THE INVENTION

As the biological action of thiol protease such as calpain, papain, cathepsin B, cathepsin H, cathepsin L. etc. has been elucidated, it has been found that the abnormal increase thereof is the cause of various diseases, so that the inhibitors of thiol protease have been used as their therapeutical agents of those diseases. For example, reports have been issued that calpain inhibitors have effects on animal models with muscular dystrophy, cataract, myocardial infarction, delayed death of neurocytes after brain infarction, and the like, while cathepsin inhibitors have effects on cancer metastasis, amyotrophy, osteoporosis and the like. However, because known inhibitors of thiol proteases, such as peptidyl aldehydes, epoxy succinate derivatives, etc., are poor in oral administration, tissue distribution, and cell membrane permeability, expectation has been toward the development of novel thiol protease inhibitors which can overcome these problems.

SUMMARY OF THE INVENTION

Thus, the present inventors have made investigations of the intermediate for the production of a thiol protease inhibitor showing excellent oral administration, tissue distribution, and cell membrane permeability. Then, the inventors have achieved the present invention.

The present invention resides in cyclopropene derivatives represented by the general formula (I):

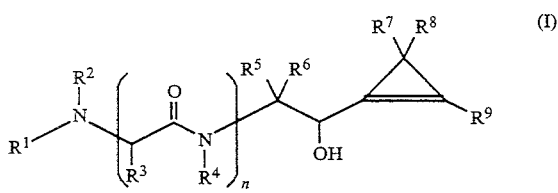

[In the above general formula (I), $R^1$ represents hydrogen atom or a protective group of amino group; $R^2$ represents hydrogen atom, a protective group of amino group or $C_1$–$C_5$ alkyl group; or when $R^1$ and $R^2$ are taken together, they represent phthaloyl group; $R^4$ and $R^6$ independently represent hydrogen atom or $C_1$–$C_5$ alkyl group; $R^3$ and $R^5$ independently represent hydrogen atom or $C_1$–$C_{15}$ alkyl group optionally substituted with $C_3$–$C_{10}$ cycloalkyl group or $C_6$–$C_{10}$ aryl group; or when $R^5$ and $R^6$ are taken together, they represent $C_2$–$C_6$ alkylene group; $R^7$ and $R^8$ represent —$OR^{10}$ and —$OR^{11}$, respectively (wherein $R^{10}$ and $R^{11}$ independently represent $C_1$–$C_5$ alkyl group optionally substituted with phenyl group: or when $R^{10}$ and $R^{11}$ are taken together, they represent $C_2$–$C_6$ alkylene group optionally substituted with one or more $C_1$–$C_5$ alkyl groups); or when $R^7$ and $R^8$ are taken together, they represent =O; $R^9$ represents hydrogen atom, $C_1$–$C_{15}$ alkyl group, $C_3$–$C_{10}$ cycloalkyl group, $C_2$–$C_{15}$ alkenyl group, $C_6$–$C_{10}$ aryl group optionally substituted with a substituent, heterocyclic group optionally substituted with a substituent, or —$CR^{12}R^{13}OH$ (wherein $R^{12}$ and $R^{13}$ independently represent hydrogen atom, $C_1$–$C_{15}$ alkyl group or $C_6$–$C_{10}$ aryl group; or when $R^{12}$ and $R^{13}$ are taken together to form $C_3$–$C_{10}$ cycloalkyl group); and n represents 0 or 1, provided that when n represents 1, $R^7$, when taken together with $R^8$ does not represent =O], and the salt thereof.

DETAILED DESCRIPTION OF THE INVENTION

The present invention will now be explained in details. The compound of the present invention is cyclopropene derivatives represented by the general formula (I):

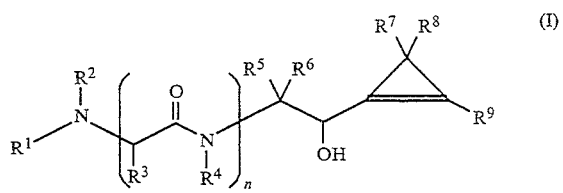

[In the above general formula (I), $R^1$ represents hydrogen atom or a protective group of amino group (urethane-type protective group such as methoxycarbonyl group, tert-butoxycarbonyl group, benzyloxycarbonyl group, 4-methoxybenzyloxycarbonyl group, 4-chlorobenzyloxycarbonyl group, 3,5-dimethoxybenzyloxycarbonyl group, 3,4,5-trimethoxybenzyloxycarbonyl group, 9-fluorenylmethoxycarbonyl group, etc.; acyl-type protective group such as formyl group, trifluoroacetyl group, p-toluene sulfonyl group, 2,4,6-trimethylbenzene sulfonyl group, benzoyl group, chloroacetyl group, etc.; alkyl-type protective group such as benzyl group, diphenylmethyl group, trityl group, etc.); $R^2$ represents hydrogen atom, a protective group of amino group (which is as defined for $R^1$) or $C_1$–$C_5$ alkyl group (methyl group, propyl group, pentyl group, etc.); or when $R^1$ and $R^2$ are taken together, they represent phthaloyl group; $R^4$ and $R^6$ independently represent hydrogen atom or $C_1$–$C_5$ alkyl group (methyl group, propyl group, pentyl group, etc.); $R^3$ and $R^5$ independently represent hydrogen atom or $C_1$–$C_{15}$ alkyl group (methyl group, hexyl group, decyl group, pentadecyl group, etc.) optionally substituted with $C_3$–$C_{10}$ cycloalkyl group (cyclopropyl group, cyclopentyl group, cyclodecyl group, etc.) or $C_6$–$C_{10}$ aryl group (phenyl group, naphtyl group, etc.); or when $R^5$ and $R^6$ are taken together, they represent $C_2$–$C_6$ alkylene group (ethylene group, tetramethylene group, hexamethylene group, etc.); $R^7$ and $R^8$ represent —$OR^{10}$ and —$OR^{11}$, respectively (wherein $R^{10}$ and $R^{11}$ independently represent $C_1$–$C_5$ alkyl group (methyl group, propyl group, pentyl group, etc.) optionally substituted with phenyl group; or when $R^{10}$ and $R^{11}$ are taken together, they represent $C_2$–$C_6$ alkylene group (ethylene group, tetramethylene group, hexamethylene group, etc.) optionally substituted with one or more $C_1$–$C_5$ alkyl groups (methyl group, propyl group, pentyl group, etc.); or when $R^7$ and $R^8$ are taken together, they represent =O; $R^9$ represents hydrogen atom; $C_1$–$C_{15}$ alkyl group (methyl group, hexyl group, decyl group, pentadecyl group, etc.); $C_3$–$C_{10}$ cycloalkyl group (cyclopropyl group, cyclopentyl group, cyclodecyl group, etc.); $C_2$–$C_{15}$ alkenyl group (vinyl group, hexenyl group, undecenyl group, pentadecenyl group, etc.); $C_6$–$C_{10}$ aryl group (phenyl group, naphtyl group, etc.) optionally substituted with one or more substituents selected from the group consisting of halogen atom (fluorine atom, chlorine atom, bromine atom, iodine atom, etc.), $C_1$–$C_5$ alkyl group (methyl group, propyl group, pentyl group, etc.), hydroxyl group and $C_1$–$C_5$ alkoxy group (methoxy group, propoxy group, pentyloxy group, etc.); a heterocyclic group having one to four hetero atoms selected from the group consisting of oxygen atom, sulfur atom and nitrogen atom with the total number of the atoms constituting the ring being in the range of from 5 to 10 (furane ring, thiophene ring, pyridine ring, pyridine oxide ring, pyrimidine ring, pyridazine ring, benzofurane ring, benzothiophene ring, quinoline ring, naphthyridine ring, etc.), and optionally substituted with one or more substituents selected from the group consisting of $C_3$–$C_{12}$ trialkylsilyl group (trimethylsilyl group, triethylsilyl group, tert-butyldimethylsilyl group, etc.), halogen atom (fluorine atom, chlorine atom, bromine atom, iodine atom, etc.), $C_1$–$C_5$ alkyl group (methyl group, propyl group, pentyl group, etc.), hydroxyl group and $C_1$–$C_5$ alkoxy group (methoxy group, propoxy group, pentyloxy group, etc.); or —$CR^{12}R^{13}OH$ (wherein $R^{12}$ and $R^{13}$ independently represent hydrogen atom, $C_1$–$C_{15}$ alkyl group (methyl group, hexyl group, decyl group, pentadecyl group, etc.) or $C_6$–$C_{10}$ aryl group (phenyl group, naphthyl group, etc.); or when $R^{12}$ and $R^{13}$ are taken to form $C_3$–$C_{10}$ cycloalkyl group (cyclopropyl group, cyclopentyl group, cyclodecyl group, etc.); and n represents 0 or 1, provided that when n represents 1, $R^7$, when taken together with $R^8$ does not represent =O], and the salt thereof.

Particularly preferable is a compound of the formula (I) in which $R^1$ represents hydrogen atom, tert-butoxycarbonyl group, benzyloxycarbonyl group, methoxycarbonyl group, 9-fluorenylmethoxycarbonyl group, p-toluene sulfonyl group, or trityl group; $R^2$, $R^4$ and $R^6$ independently represent hydrogen atom or $C_1$–$C_3$ alkyl group; or when $R^1$ and $R^2$ are taken together, they represent phthaloyl group; $R^3$ and $R^5$ independently represent hydrogen atom or $C_1$–$C_5$ alkyl group optionally substituted with $C_1$–$C_5$ cycloalkyl group, phenyl group or naphtyl group; or $R^5$, when taken together with $R^6$ represents $C_3$–$C_6$ cycloalkyl group; $R^7$ and $R^8$ represent -$OR^{10}$ and —$OR^{11}$, respectively (wherein $R^{10}$ and $R^{11}$ independently represent $C_1$–$C_3$ alkyl group optionally substituted with phenyl group; or $R^{10}$, when taken together with $R^{11}$ represents $C_2$–$C_4$ alkylene group optionally substituted with one or more $C_1$–$C_3$ alkyl groups; or $R^7$,when taken together with $R^8$ represents =O;$R^9$ represents hydrogen atom; $C_1$–$C_6$ alkyl group; $C_3$–$C_8$ cycloalkyl group; $C_2$–$C_8$ alkenyl group; phenyl group or naphtyl group each optionally substituted with one or more substituents selected from the group consisting of halogen atom, $C_1$–$C_5$ alkyl group and $C_1$–$C_5$ alkoxy group; heterocyclic group having one to four hetero atoms selected from the group consisting of oxygen atom, sulfur atom and nitrogen atom with the total number of the atoms constituting the ring being in the range of from 5 to 10, and optionally substituted with one or more substituents selected from the group consisting of halogen atom, $C_1$–$C_5$ alkyl group, $C_1$–$C_5$ alkoxy group and $C_3$–$C_{12}$ trialkylsilyl group; or —$CR^{12}R^{13}OH$ (wherein $R^{12}$ and $R^{13}$ independently represent hydrogen atom, $C_1$–$C_3$ alkyl group or phenyl group); and n represents 0 or 1, provided that when n represents 1, $R^7$, when taken together with $R^8$ does not represent =O.

Most preferable is a compound of the formula (I) in which $R^1$ represents hydrogen atom, tert-butoxycarbonyl group, benzyloxycarbonyl group or methoxycarbonyl group; $R^2$, $R^4$ and $R^6$ independently represent hydrogen atom or $C_1$–$C_3$ alkyl group; $R^3$ and $R^5$ independently represent hydrogen atom or $C_1$–$C_5$ alkyl group optionally substituted with phenyl group; $R^7$ and $R^8$ represent —$OR^{10}$ and —$OR^{11}$, respectively (wherein $R^{10}$, when taken together with $R^{11}$ represents $C_2$–$C_4$ alkylene group optionally substituted with one or more substituents selected from $C_1$–$C_3$ alkyl groups; or $R^7$, when taken together with $R^8$ represents =O; $R^9$ represents hydrogen atom; $C_1$–$C_6$ alkyl group; $C_2$–$C_8$ alkenyl group; phenyl group optinally substituted with one or more substituents selected from the group consisting of halogen atom and $C_1$–$C_5$ alkyl group; furyl group or thienyl group each optionally substituted with one or more $C_3$–$C_{12}$ trialkylsilyl groups; or —$CR^{12}R^{13}OH$ (wherein $R^{12}$ and $R^{13}$ independently represent hydrogen atom, $C_1$–$C_3$ alkyl group or phenyl group); and n represents 0 or 1, provided that when n represents 1, $R^7$, when taken together with $R^8$ does not represent =O.

The asymmetric carbons present in the cyclopropene derivatives represented by the above general formula (I) independently form (R), (S) or (RS) configuration.

Specific examples of the compounds in accordance with the present invention are shown in tables. Table 1 shows the compounds wherein $R^7$ and $R^8$ represent —$OR^{10}$ and —$OR^{11}$, respectively, and n is zero; Table 2 shows the compounds wherein $R^7$,taken together with $R^8$ represents =O, and n is zero; Table 3 shows the compounds wherein n is one and $R^7$ and $R^8$ represent —$OR^{10}$ and —$OR^{11}$, respectively. In the Tables 1, 2 and 3, Boc represents tert-butoxycarbonyl group; Z represents benzyloxycarbonyl group; pMZ represents 4-methoxybenzyloxycarbonyl group; Moc represents methoxycarbonyl group; Fmoc represents 9-fluorenylmethoxycarbonyl group; Tfa represents trifluoroacetyl group; Tos represents p-toluene sulfonyl group; Mts represents 2,4,6-trimethylbenzene sulfonyl group; Trt represents trityl group; and Pht represents phthalyl group.

TABLE 1

| Comp. No. | $R^1$ | $R^2$ | $R^5$ | $R^6$ | $R^{10}$ | $R^{11}$ | $R^9$ |
|---|---|---|---|---|---|---|---|
| 1 | Boc | H | H | H | 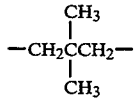 | | H |

TABLE 1-continued

| Comp. No. | $R^1$ | $R^2$ | $R^5$ | $R^6$ | $R^{10}$ | $R^{11}$ | $R^9$ |
|---|---|---|---|---|---|---|---|
| 2 | Boc | H | —CH₃ | H | —CH₂C(CH₃)₂CH₂— | | H |
| 3 | Boc | H | —CH(CH₃)₂ | H | —CH₂C(CH₃)₂CH₂— | | H |
| 4 | Z | H | —CH(CH₃)₂ | H | —CH₂C(CH₃)₂CH₂— | | H |
| 5 | Boc | H | —CH₂CH₂CH₃ | H | —CH₂C(CH₃)₂CH₂— | | H |
| 6 | Boc | H | —CH₂CH(CH₃)₂ | H | —CH₂C(CH₃)₂CH₂— | | H |
| 7 | Boc | —CH₃ | —CH₂CH(CH₃)₂ | H | —CH₂C(CH₃)₂CH₂— | | H |
| 8 | Boc | H | —CH(CH₃)CH₂CH₃ | H | —CH₂C(CH₃)₂CH₂— | | H |
| 9 | Boc | H | —CH₂CH₂CH₂CH₃ | H | —CH₃ | —CH₃ | H |
| 10 | Boc | H | —CH₂CH₂CH₂CH₃ | H | —CH₂CH₃ | —CH₂CH₃ | H |
| 11 | Boc | H | —CH₂CH₂CH₂CH₃ | H | —CH₂C₆H₅ | —CH₂C₆H₅ | H |
| 12 | Boc | H | —CH₂CH₂CH₂CH₃ | H | —CH₂CH₂— | | H |
| 13 | Boc | H | —CH₂CH₂CH₂CH₃ | H | —CH₂CH₂CH₂— | | H |
| 14 | Boc | H | —CH₂CH₂CH₂CH₃ | H | —CH₂C(CH₃)₂CH₂— | | H |
| 15 | Boc | H | —CH₂CH₂CH₂CH₃ | H | —CH(CH₃)CH₂CH(CH₃)— | | H |
| 16 | Z | H | —CH₂CH₂CH₂CH₃ | H | —CH₂C(CH₃)₂CH₂— | | H |
| 17 | pMZ | H | —CH₂CH₂CH₂CH₃ | H | —CH₂C(CH₃)₂CH₂— | | H |
| 18 | Fmoc | H | —CH₂CH₂CH₂CH₃ | H | —CH₂C(CH₃)₂CH₂— | | H |

TABLE 1-continued

| Comp. No. | R¹ | R² | R⁵ | R⁶ | R¹⁰ | R¹¹ | R⁹ |
|---|---|---|---|---|---|---|---|
| 19 | Tos | H | —CH₂CH₂CH₂CH₃ | H | | —CH₂C(CH₃)₂CH₂— | H |
| 20 | Mts | H | —CH₂CH₂CH₂CH₃ | H | | —CH₂C(CH₃)₂CH₂— | H |
| 21 | Trt | H | —CH₂CH₂CH₂CH₃ | H | | —CH₂C(CH₃)₂CH₂— | H |
| 22 | Pht | | —CH₂CH₂CH₂CH₃ | H | | —CH₂C(CH₃)₂CH₂— | H |
| 23 | Boc | H | —CH₂-cyclohexyl | H | | —CH₂C(CH₃)₂CH₂— | H |
| 24 | Boc | H | —CH₂-phenyl | H | | —CH₂C(CH₃)₂CH₂— | H |
| 25 | Boc | H | —CH₂-(1-naphthyl) | H | | —CH₂C(CH₃)₂CH₂— | H |
| 26 | Boc | H | —CH₂-(2-naphthyl) | H | | —CH₂C(CH₃)₂CH₂— | H |
| 27 | Boc | H | —CH₃ | —CH₃ | | —CH₂C(CH₃)₂CH₂— | H |
| 28 | Boc | H | —CH₂CH₃ | —CH₂CH₃ | | —CH₂C(CH₃)₂CH₂— | H |
| 29 | Boc | H | —CH₂CH₂CH₂CH₂— | | | —CH₂C(CH₃)₂CH₂— | H |
| 30 | Boc | H | —CH₂CH₂CH₂CH₂CH₂— | | | —CH₂C(CH₃)₂CH₂— | H |

TABLE 1-continued

| Comp. No. | R¹ | R² | R⁵ | R⁶ | R¹⁰ | R¹¹ | R⁹ |
|---|---|---|---|---|---|---|---|
| 31 | Boc | H | —CH₂CH(CH₃)₂ | H | | —CH₂C(CH₃)₂CH₂— | —CH₃ |
| 32 | Boc | H | —CH₂CH₂CH₂CH₃ | H | | —CH₂C(CH₃)₂CH₂— | —CH₃ |
| 33 | Boc | H | —CH₂C₆H₅ | H | | —CH₂C(CH₃)₂CH₂— | —CH₃ |
| 34 | Boc | H | —CH₂CH(CH₃)₂ | H | | —CH₂C(CH₃)₂CH₂— | —CH₂CH₃ |
| 35 | Boc | H | —CH₂CH₂CH₂CH₃ | H | | —CH₂C(CH₃)₂CH₂— | —CH₂CH₃ |
| 36 | Boc | H | —CH₂C₆H₅ | H | | —CH₂C(CH₃)₂CH₂— | —CH₂CH₃ |
| 37 | Boc | H | —CH₂CH(CH₃)₂ | H | | —CH₂C(CH₃)₂CH₂— | —CH(CH₃)₂ |
| 38 | Boc | H | —CH₂CH₂CH₂CH₃ | H | | —CH₂C(CH₃)₂CH₂— | —CH(CH₃)₂ |
| 39 | Boc | H | —CH₂C₆H₅ | H | | —CH₂C(CH₃)₂CH₂— | —CH(CH₃)₂ |
| 40 | Boc | H | —CH₂CH(CH₃)₂ | H | | —CH₂C(CH₃)₂CH₂— | —CH₂CH₂CH(CH₃)₂ |
| 41 | Boc | H | —CH₂CH₂CH₂CH₃ | H | | —CH₂C(CH₃)₂CH₂— | —CH₂CH₂CH(CH₃)₂ |
| 42 | Boc | H | —CH₂C₆H₅ | H | | —CH₂C(CH₃)₂CH₂— | —CH₂CH₂CH(CH₃)₂ |
| 43 | Boc | H | —CH₂CH(CH₃)₂ | H | | —CH₂C(CH₃)₂CH₂— | —C₆H₁₁ |

TABLE 1-continued

| Comp. No. | $R^1$ | $R^2$ | $R^5$ | $R^6$ | $R^{10}$ | $R^{11}$ | $R^9$ |
|---|---|---|---|---|---|---|---|
| 44 | Boc | H | —CH₂CH₂CH₂CH₃ | H | —CH₂C(CH₃)₂CH₂— | | cyclohexyl |
| 45 | Boc | H | —CH₂—C₆H₅ | H | —CH₂C(CH₃)₂CH₂— | | cyclohexyl |
| 46 | Boc | H | —CH₂CH(CH₃)₂ | H | —CH₂C(CH₃)₂CH₂— | | —CH=CH₂ |
| 47 | Boc | H | —CH₂CH₂CH₂CH₃ | H | —CH₂C(CH₃)₂CH₂— | | —CH=CH₂ |
| 48 | Boc | H | —CH₂—C₆H₅ | H | —CH₂C(CH₃)₂CH₂— | | —CH=CH₂ |
| 49 | Boc | H | —CH₂CH(CH₃)₂ | H | —CH₂C(CH₃)₂CH₂— | | —CH=CH(CH₂)₃CH₃ (trans) |
| 50 | Boc | H | —CH₂CH₂CH₂CH₃ | H | —CH₂C(CH₃)₂CH₂— | | —CH=CH(CH₂)₃CH₃ (trans) |
| 51 | Boc | H | —CH₂—C₆H₅ | H | —CH₂C(CH₃)₂CH₂— | | —CH=CH(CH₂)₃CH₃ (trans) |
| 52 | Boc | H | —CH₂CH(CH₃)₂ | H | —CH₂C(CH₃)₂CH₂— | | —CH=CH(CH₂)₃CH₃ (cis) |
| 53 | Boc | H | —CH₂CH₂CH₂CH₃ | H | —CH₂C(CH₃)₂CH₂— | | —CH=CH(CH₂)₃CH₃ (cis) |
| 54 | Boc | H | —CH₂—C₆H₅ | H | —CH₂C(CH₃)₂CH₂— | | —CH=CH(CH₂)₃CH₃ (cis) |
| 55 | Boc | H | —CH₂CH(CH₃)₂ | H | —CH₂C(CH₃)₂CH₂— | | —CH₂—CH=CH₂ |
| 56 | Boc | H | —CH₂CH₂CH₂CH₃ | H | —CH₂C(CH₃)₂CH₂— | | —CH₂—CH=CH₂ |

TABLE 1-continued

| Comp. No. | R¹ | R² | R⁵ | R⁶ | R¹⁰ | R¹¹ | R⁹ |
|---|---|---|---|---|---|---|---|
| 57 | Boc | H | —CH₂—C₆H₅ | H | | —CH₂CCH₂— with CH₃, CH₃ | —CH₂—CH=CH₂ |
| 58 | Boc | H | H | H | | —CH₂CCH₂— with CH₃, CH₃ | C₆H₅ |
| 59 | Boc | H | —CH₃ | H | | —CH₂CCH₂— with CH₃, CH₃ | C₆H₅ |
| 60 | Boc | H | —CH(CH₃)₂ | H | —CH₃ | —CH₃ | C₆H₅ |
| 61 | Boc | H | —CH(CH₃)₂ | H | —CH₂CH₃ | —CH₂CH₃ | C₆H₅ |
| 62 | Boc | H | —CH(CH₃)₂ | H | —CH₂—C₆H₅ | —CH₂—C₆H₅ | C₆H₅ |
| 63 | Boc | H | —CH(CH₃)₂ | H | —CH₂CH₂— | | C₆H₅ |
| 64 | Boc | H | —CH(CH₃)₂ | H | —CH₂CH₂CH₂— | | C₆H₅ |
| 65 | Boc | H | —CH(CH₃)₂ | H | —CH₂CCH₂— with CH₃, CH₃ | | C₆H₅ |
| 66 | Boc | H | —CH(CH₃)₂ | H | —CHCH₂CH— with CH₃, CH₃ | | C₆H₅ |
| 67 | Z | H | —CH(CH₃)₂ | H | | —CH₂CCH₂— with CH₃, CH₃ | C₆H₅ |
| 68 | pMZ | H | —CH(CH₃)₂ | H | | —CH₂CCH₂— with CH₃, CH₃ | C₆H₅ |
| 69 | Fmoc | H | —CH(CH₃)₂ | H | | —CH₂CCH₂— with CH₃, CH₃ | C₆H₅ |

TABLE 1-continued

| Comp. No. | $R^1$ | $R^2$ | $R^5$ | $R^6$ | $R^{10}$ | $R^{11}$ | $R^9$ |
|---|---|---|---|---|---|---|---|
| 70 | Tos | H | —CH(CH$_3$)$_2$ | H | | —CH$_2$C(CH$_3$)$_2$CH$_2$— | Ph |
| 71 | Mts | H | —CH(CH$_3$)$_2$ | H | | —CH$_2$C(CH$_3$)$_2$CH$_2$— | Ph |
| 72 | Trt | H | —CH(CH$_3$)$_2$ | H | | —CH$_2$C(CH$_3$)$_2$CH$_2$— | Ph |
| 73 | Pht | | —CH(CH$_3$)$_2$ | H | | —CH$_2$C(CH$_3$)$_2$CH$_2$— | Ph |
| 74 | Boc | —CH$_3$ | —CH(CH$_3$)$_2$ | H | | —CH$_2$C(CH$_3$)$_2$CH$_2$— | Ph |
| 75 | Boc | H | —CH$_2$CH(CH$_3$)$_2$ | H | | —CH$_2$C(CH$_3$)$_2$CH$_2$— | Ph |
| 76 | Boc | H | —CH$_2$CH$_2$CH$_2$CH$_3$ | H | | —CH$_2$C(CH$_3$)$_2$CH$_2$— | Ph |
| 77 | Boc | —CH$_3$ | —CH$_2$CH$_2$CH$_2$CH$_3$ | H | | —CH$_2$C(CH$_3$)$_2$CH$_2$— | Ph |
| 78 | Boc | H | —CH$_2$-cyclohexyl | H | | —CH$_2$C(CH$_3$)$_2$CH$_2$— | Ph |
| 79 | Boc | H | —CH$_2$-phenyl | H | | —CH$_2$C(CH$_3$)$_2$CH$_2$— | Ph |
| 80 | Boc | H | —CH$_2$-(1-naphthyl) | H | | —CH$_2$C(CH$_3$)$_2$CH$_2$— | Ph |
| 81 | Boc | H | —CH$_2$-(2-naphthyl) | H | | —CH$_2$C(CH$_3$)$_2$CH$_2$— | Ph |

TABLE 1-continued

| Comp. No. | R¹ | R² | R⁵ | R⁶ | R¹⁰ | R¹¹ | R⁹ |
|---|---|---|---|---|---|---|---|
| 82 | Boc | H | —CH₃ | —CH₃ | | —CH₂CCH₂—<br>with CH₃, CH₃ | phenyl |
| 83 | Boc | H | —CH₂CH₃ | —CH₂CH₃ | | —CH₂CCH₂—<br>with CH₃, CH₃ | phenyl |
| 84 | Boc | H | —CH₂CH₂CH₂CH₂— | | | —CH₂CCH₂—<br>with CH₃, CH₃ | phenyl |
| 85 | Boc | H | —CH₂CH₂CH₂CH₂CH₂— | | | —CH₂CCH₂—<br>with CH₃, CH₃ | phenyl |
| 86 | Boc | H | —CH(CH₃)₂ | H | | —CH₂CCH₂—<br>with CH₃, CH₃ | 2-F-phenyl |
| 87 | Boc | H | —CH₂CH₂CH₂CH₃ | H | | —CH₂CCH₂—<br>with CH₃, CH₃ | 2-F-phenyl |
| 88 | Boc | H | —CH(CH₃)₂ | H | | —CH₂CCH₂—<br>with CH₃, CH₃ | 2-F-phenyl |
| 89 | Boc | H | —CH₂CH₂CH₂CH₃ | H | | —CH₂CCH₂—<br>with CH₃, CH₃ | 2-F-phenyl |
| 90 | Boc | H | —CH(CH₃)₂ | H | | —CH₂CCH₂—<br>with CH₃, CH₃ | 4-F-phenyl |
| 91 | Boc | H | —CH₂CH₂CH₂CH₃ | H | | —CH₂CCH₂—<br>with CH₃, CH₃ | 4-F-phenyl |
| 92 | Boc | H | —CH(CH₃)₂ | H | | —CH₂CCH₂—<br>with CH₃, CH₃ | 2-Cl-phenyl |
| 93 | Boc | H | —CH₂CH₂CH₂CH₃ | H | | —CH₂CCH₂—<br>with CH₃, CH₃ | 2-Cl-phenyl |

TABLE 1-continued

| Comp. No. | R¹ | R² | R⁵ | R⁶ | R¹⁰ | R¹¹ | R⁹ |
|---|---|---|---|---|---|---|---|
| 94 | Boc | H | —CH(CH₃)₂ | H | | —CH₂C(CH₃)₂CH₂— | 3-Cl-C₆H₄ |
| 95 | Boc | H | —CH₂CH₂CH₂CH₃ | H | | —CH₂C(CH₃)₂CH₂— | 3-Cl-C₆H₄ |
| 96 | Boc | H | —CH(CH₃)₂ | H | | —CH₂C(CH₃)₂CH₂— | 4-Cl-C₆H₄ |
| 97 | Boc | H | —CH₂CH₂CH₂CH₃ | H | | —CH₂C(CH₃)₂CH₂— | 4-Cl-C₆H₄ |
| 98 | Boc | H | —CH(CH₃)₂ | H | | —CH₂C(CH₃)₂CH₂— | 2-OCH₃-C₆H₄ |
| 99 | Boc | H | —CH₂CH₂CH₂CH₃ | H | | —CH₂C(CH₃)₂CH₂— | 2-OCH₃-C₆H₄ |
| 100 | Boc | H | —CH(CH₃)₂ | H | | —CH₂C(CH₃)₂CH₂— | 3-OCH₃-C₆H₄ |
| 101 | Boc | H | —CH₂CH₂CH₂CH₃ | H | | —CH₂C(CH₃)₂CH₂— | 3-OCH₃-C₆H₄ |
| 102 | Boc | H | —CH(CH₃)₂ | H | | —CH₂C(CH₃)₂CH₂— | 4-OCH₃-C₆H₄ |
| 103 | Boc | H | —CH₂CH₂CH₂CH₃ | H | | —CH₂C(CH₃)₂CH₂— | 4-OCH₃-C₆H₄ |
| 104 | Boc | H | —CH(CH₃)₂ | H | | —CH₂C(CH₃)₂CH₂— | 2-CH₃-C₆H₄ |
| 105 | Boc | H | —CH₂CH₂CH₂CH₃ | H | | —CH₂C(CH₃)₂CH₂— | 2-CH₃-C₆H₄ |

TABLE 1-continued

| Comp. No. | R¹ | R² | R⁵ | R⁶ | R¹⁰ | R¹¹ | R⁹ |
|---|---|---|---|---|---|---|---|
| 106 | Boc | H | —CH(CH₃)₂ | H | | —CH₂C(CH₃)₂CH₂— | 3-methylphenyl (m-tolyl with extra CH₃) |
| 107 | Boc | H | —CH₂CH₂CH₂CH₃ | H | | —CH₂C(CH₃)₂CH₂— | 3,5-dimethylphenyl |
| 108 | Boc | H | —CH(CH₃)₂ | H | | —CH₂C(CH₃)₂CH₂— | 2,4-dimethylphenyl |
| 109 | Boc | H | —CH₂CH₂CH₂CH₃ | H | | —CH₂C(CH₃)₂CH₂— | 2,4-dimethylphenyl |
| 110 | Boc | H | —CH₃ | H | | —CH₂C(CH₃)₂CH₂— | 1-naphthyl |
| 111 | Boc | H | —CH(CH₃)₂ | H | | —CH₂C(CH₃)₂CH₂— | 1-naphthyl |
| 112 | Boc | H | —CH₂CH(CH₃)₂ | H | | —CH₂C(CH₃)₂CH₂— | 1-naphthyl |
| 113 | Boc | H | —CH₂CH₂CH₂CH₃ | H | | —CH₂C(CH₃)₂CH₂— | 1-naphthyl |
| 114 | Boc | H | —CH₃ | H | | —CH₂C(CH₃)₂CH₂— | 2-naphthyl |
| 115 | Boc | H | —CH(CH₃)₂ | H | | —CH₂C(CH₃)₂CH₂— | 2-naphthyl |

TABLE 1-continued

| Comp. No. | R¹ | R² | R⁵ | R⁶ | R¹⁰ | R¹¹ | R⁹ |
|---|---|---|---|---|---|---|---|
| 116 | Boc | H | —CH₂CH(CH₃)₂ | H | | —CH₂C(CH₃)₂CH₂— | 2-naphthyl |
| 117 | Boc | H | —CH₂CH₂CH₂CH₃ | H | | —CH₂C(CH₃)₂CH₂— | 2-naphthyl |
| 118 | Boc | H | —CH(CH₃)₂ | H | | —CH₂C(CH₃)₂CH₂— | 2-furyl |
| 119 | Boc | H | —CH₂CH₂CH₂CH₃ | H | | —CH₂C(CH₃)₂CH₂— | 2-furyl |
| 120 | Boc | H | —CH(CH₃)₂ | H | | —CH₂C(CH₃)₂CH₂— | 3-methyl-2-furyl |
| 121 | Boc | H | —CH₂CH₂CH₂CH₃ | H | | —CH₂C(CH₃)₂CH₂— | 3-methyl-2-furyl |
| 122 | Boc | H | —CH(CH₃)₂ | H | | —CH₂C(CH₃)₂CH₂— | 5-chloro-2-furyl |
| 123 | Boc | H | —CH₂CH₂CH₂CH₃ | H | | —CH₂C(CH₃)₂CH₂— | 5-chloro-2-furyl |
| 124 | Boc | H | —CH(CH₃)₂ | H | | —CH₂C(CH₃)₂CH₂— | 5-methyl-2-furyl |
| 125 | Boc | H | —CH₂CH₂CH₂CH₃ | H | | —CH₂C(CH₃)₂CH₂— | 5-methyl-2-furyl |
| 126 | Boc | H | —CH(CH₃)₂ | H | | —CH₂C(CH₃)₂CH₂— | 4-methyl-2-furyl |
| 127 | Boc | H | —CH₂CH₂CH₂CH₃ | H | | —CH₂C(CH₃)₂CH₂— | 4-methyl-2-furyl |

TABLE 1-continued

| Comp. No. | R¹ | R² | R⁵ | R⁶ | R¹⁰ | R¹¹ | R⁹ |
|---|---|---|---|---|---|---|---|
| 128 | Boc | H | —CH(CH$_3$)$_2$ | H | | —CH$_2$C(CH$_3$)$_2$CH$_3$ | 5-(trimethylsilyl)furan-2-yl |
| 129 | Boc | H | —CH$_2$CH(CH$_3$)$_2$ | H | | —CH$_2$C(CH$_3$)$_2$CH$_3$ | 5-(trimethylsilyl)furan-2-yl |
| 130 | Boc | H | —CH$_2$CH$_2$CH$_2$CH$_3$ | H | | —CH$_2$C(CH$_3$)$_2$CH$_3$ | 5-(trimethylsilyl)furan-2-yl |
| 131 | Boc | H | —CH(CH$_3$)$_2$ | H | | —CH$_2$C(CH$_3$)$_2$CH$_3$ | thien-2-yl |
| 132 | Boc | H | —CH$_2$CH$_2$CH$_2$CH$_3$ | H | | —CH$_2$C(CH$_3$)$_2$CH$_3$ | thien-2-yl |
| 133 | Boc | H | —CH(CH$_3$)$_2$ | H | | —CH$_2$C(CH$_3$)$_2$CH$_3$ | 4-methylthien-3-yl |
| 134 | Boc | H | —CH$_2$CH$_2$CH$_2$CH$_3$ | H | | —CH$_2$C(CH$_3$)$_2$CH$_3$ | 4-methylthien-3-yl |
| 135 | Boc | H | —CH(CH$_3$)$_2$ | H | | —CH$_2$C(CH$_3$)$_2$CH$_3$ | 5-chlorothien-2-yl |
| 136 | Boc | H | —CH$_2$CH$_2$CH$_2$CH$_3$ | H | | —CH$_2$C(CH$_3$)$_2$CH$_3$ | 5-chlorothien-2-yl |
| 137 | Boc | H | —CH(CH$_3$)$_2$ | H | | —CH$_2$C(CH$_3$)$_2$CH$_3$ | 5-(trimethylsilyl)thien-2-yl |
| 138 | Boc | H | —CH$_2$CH(CH$_3$)$_2$ | H | | —CH$_2$C(CH$_3$)$_2$CH$_3$ | 5-(trimethylsilyl)thien-2-yl |
| 139 | Boc | H | —CH$_2$CH$_2$CH$_2$CH$_3$ | H | | —CH$_2$C(CH$_3$)$_2$CH$_3$ | 5-(trimethylsilyl)thien-2-yl |
| 140 | Boc | H | —CH(CH$_3$)$_2$ | H | | —CH$_2$C(CH$_3$)$_2$CH$_3$ | —CH$_2$OH |
| 141 | Boc | H | —CH$_2$CH$_2$CH$_2$CH$_3$ | H | | —CH$_2$C(CH$_3$)$_2$CH$_3$ | —CH$_2$OH |

TABLE 1-continued

| Comp. No. | $R^1$ | $R^2$ | $R^5$ | $R^6$ | $R^{10}$ | $R^{11}$ | $R^9$ |
|---|---|---|---|---|---|---|---|
| 142 | Boc | H | —CH(CH$_3$)$_2$ | H | | —CH$_2$C(CH$_3$)$_2$CH$_2$— | —CH(CH$_3$)OH |
| 143 | Boc | H | —CH$_2$CH$_2$CH$_2$CH$_3$ | H | | —CH$_2$C(CH$_3$)$_2$CH$_2$— | —CH(CH$_3$)OH |
| 144 | Boc | H | —CH(CH$_3$)$_2$ | H | | —CH$_2$C(CH$_3$)$_2$CH$_2$— | —CH(OH)(CH$_2$)$_3$CH$_3$ |
| 145 | Boc | H | —CH$_2$CH$_2$CH$_2$CH$_3$ | H | | —CH$_2$C(CH$_3$)$_2$CH$_2$— | —CH(OH)(CH$_2$)$_3$CH$_3$ |
| 146 | Boc | H | —CH$_3$ | H | | —CH$_2$C(CH$_3$)$_2$CH$_2$— | —C(CH$_3$)$_2$OH |
| 147 | Boc | H | —CH(CH$_3$)$_2$ | H | | —CH$_2$C(CH$_3$)$_2$CH$_2$— | —C(CH$_3$)$_2$OH |
| 148 | Z | H | —CH(CH$_3$)$_2$ | H | | —CH$_2$C(CH$_3$)$_2$CH$_2$— | —C(CH$_3$)$_2$OH |
| 149 | Fmoc | H | —CH(CH$_3$)$_2$ | H | | —CH$_2$C(CH$_3$)$_2$CH$_2$— | —C(CH$_3$)$_2$OH |
| 150 | Boc | H | —CH$_2$CH(CH$_3$)$_2$ | H | | —CH$_2$C(CH$_3$)$_2$CH$_2$— | —C(CH$_3$)$_2$OH |
| 151 | Boc | H | —CH(CH$_3$)CH$_2$CH$_3$ | H | | —CH$_2$C(CH$_3$)$_2$CH$_2$— | —C(CH$_3$)$_2$OH |
| 152 | Boc | H | —CH$_2$CH$_2$CH$_2$CH$_3$ | H | | —CH$_2$C(CH$_3$)$_2$CH$_2$— | —C(CH$_3$)$_2$OH |
| 153 | Boc | H | —CH$_2$-cyclohexyl | H | | —CH$_2$C(CH$_3$)$_2$CH$_2$— | —C(CH$_3$)$_2$OH |
| 154 | Boc | H | —CH$_2$-phenyl | H | | —CH$_2$C(CH$_3$)$_2$CH$_2$— | —C(CH$_3$)$_2$OH |

TABLE 1-continued

| Comp. No. | R¹ | R² | R⁵ | R⁶ | R¹⁰ | R¹¹ | R⁹ |
|---|---|---|---|---|---|---|---|
| 155 | Boc | H | —CH₃ | H | | —CH₂C(CH₃)₂CH₂— | 1-phenylethan-1-ol (CH(OH)CH₃-phenyl) |
| 156 | Boc | H | —CH(CH₃)₂ | H | | —CH₂C(CH₃)₂CH₂— | 1-phenylethan-1-ol |
| 157 | Boc | H | —CH₂CH(CH₃)₂ | H | | —CH₂C(CH₃)₂CH₂— | 1-phenylethan-1-ol |
| 158 | Boc | H | —CH₂CH₂CH₂CH₃ | H | | —CH₂C(CH₃)₂CH₂— | 1-phenylethan-1-ol |
| 159 | Boc | H | —CH(CH₃)₂ | H | | —CH₂C(CH₃)₂CH₂— | 2-phenylpropan-2-ol (C(CH₃)(OH)-phenyl) |
| 160 | Boc | H | —CH₂CH₂CH₂CH₃ | H | | —CH₂C(CH₃)₂CH₂— | 2-phenylpropan-2-ol |
| 161 | Moc | H | —CH(CH₃)₂ | H | | —CH₂C(CH₃)₂CH₂— | phenyl |
| 162 | Moc | H | —CH₂CH₂CH₂CH₃ | H | | —CH₂C(CH₃)₂CH₂— | phenyl |

TABLE 2

| Comp. No. | R¹ | R² | R⁵ | R⁶ | R⁹ |
|---|---|---|---|---|---|
| 163 | Boc | H | H | —H | —H |
| 164 | H | H | H | —H | —H |
| 165 | Boc | H | —CH₃ | —H | —H |
| 166 | H | H | —CH₃ | —H | —H |
| 167 | Boc | H | —CH(CH₃)₂ | —H | —H |
| 168 | H | H | —CH(CH₃)₂ | —H | —H |
| 169 | Z | H | —CH(CH₃)₂ | —H | —H |
| 170 | Boc | H | —CH₂CH₂CH₃ | —H | —H |
| 171 | H | H | —CH₂CH₂CH₃ | —H | —H |
| 172 | Boc | H | —CH₂CH(CH₃)₂ | —H | —H |
| 173 | H | H | —CH₂CH(CH₃)₂ | —H | —H |
| 174 | Boc | —CH₃ | —CH₂CH(CH₃)₂ | —H | —H |
| 175 | H | —CH₃ | —CH₂CH(CH₃)₂ | —H | —H |
| 176 | Boc | H | —CH(CH₃)CH₂CH₃ | —H | —H |

TABLE 2-continued

| Comp. No. | R¹ | R² | R⁵ | R⁶ | R⁹ |
|---|---|---|---|---|---|
| 177 | H | H | —CH(CH₃)CH₂CH₃ | —H | —H |
| 178 | Boc | H | —CH₂CH₂CH₂CH₃ | —H | —H |
| 179 | H | H | —CH₂CH₂CH₂CH₃ | —H | —H |
| 180 | Z | H | —CH₂CH₂CH₂CH₃ | —H | —H |
| 181 | pMZ | H | —CH₂CH₂CH₂CH₃ | —H | —H |
| 182 | Fmoc | H | —CH₂CH₂CH₂CH₃ | —H | —H |
| 183 | Tos | H | —CH₂CH₂CH₂CH₃ | —H | —H |
| 184 | Mts | H | —CH₂CH₂CH₂CH₃ | —H | —H |
| 185 | Trt | H | —CH₂CH₂CH₂CH₃ | —H | —H |
| 186 |  | Pht | —CH₂CH₂CH₂CH₃ | —H | —H |
| 187 | Boc | H | —CH₂-cyclohexyl | —H | —H |
| 188 | H | H | —CH₂-cyclohexyl | —H | —H |
| 189 | Boc | H | —CH₂-phenyl | —H | —H |
| 190 | H | H | —CH₂-phenyl | —H | —H |
| 191 | Boc | H | —CH₂-(1-naphthyl) | —H | —H |
| 192 | H | H | —CH₂-(1-naphthyl) | —H | —H |
| 193 | Boc | H | —CH₂-(2-naphthyl) | —H | —H |
| 194 | H | H | —CH₂-(2-naphthyl) | —H | —H |
| 195 | Boc | H | —CH₃ | —CH₃ | —H |
| 196 | H | H | —CH₃ | —CH₃ | —H |
| 197 | Boc | H | —CH₂CH₃ | —CH₂CH₃ | —H |
| 198 | H | H | —CH₂CH₃ | —CH₂CH₃ | —H |
| 199 | Boc | H | —CH₂CH₂CH₂CH₂— | | —H |
| 200 | H | H | —CH₂CH₂CH₂CH₂— | | —H |

TABLE 2-continued

| Comp. No. | R¹ | R² | R⁵ | R⁶ | R⁹ |
|---|---|---|---|---|---|
| 201 | Boc | H | —CH₂CH₂CH₂CH₂CH₂— | | —H |
| 202 | H | H | —CH₂CH₂CH₂CH₂CH₂— | | —H |
| 203 | Boc | H | —CH₂CH(CH₃)₂ | —H | —CH₃ |
| 204 | H | H | —CH₂CH(CH₃)₂ | —H | —CH₃ |
| 205 | Boc | H | —CH₂CH₂CH₂CH₃ | —H | —CH₃ |
| 206 | H | H | —CH₂CH₂CH₂CH₃ | —H | —CH₃ |
| 207 | Boc | H | —CH₂—C₆H₅ 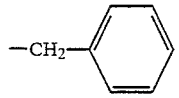 | —H | —CH₃ |
| 208 | H | H | —CH₂—C₆H₅ 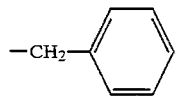 | —H | —CH₃ |
| 209 | Boc | H | —CH₂CH(CH₃)₂ | —H | —CH₂CH₃ |
| 210 | H | H | —CH₂CH(CH₃)₂ | —H | —CH₂CH₃ |
| 211 | Boc | H | —CH₂CH₂CH₂CH₃ | —H | —CH₂CH₃ |
| 212 | H | H | —CH₂CH₂CH₂CH₃ | —H | —CH₂CH₃ |
| 213 | Boc | H | —CH₂—C₆H₅ 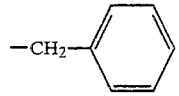 | —H | —CH₂CH₃ |
| 214 | H | H | —CH₂—C₆H₅ 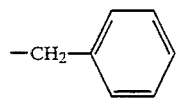 | —H | —CH₂CH₃ |
| 215 | Boc | H | —CH₂CH(CH₃)₂ | —H | —CH(CH₃)₂ |
| 216 | H | H | —CH₂CH(CH₃)₂ | —H | —CH(CH₃)₂ |
| 217 | Boc | H | —CH₂CH(CH₃)₂ | —H | —CH(CH₃)₂ |
| 218 | H | H | —CH₂CH(CH₃)₂ | —H | —CH(CH₃)₂ |
| 219 | Boc | H | —CH₂—C₆H₅ 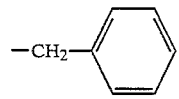 | —H | —CH(CH₃)₂ |
| 220 | H | H | —CH₂—C₆H₅ 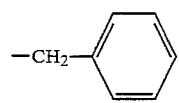 | —H | —CH(CH₃)₂ |
| 221 | Boc | H | —CH₂CH(CH₃)₂ | —H | —CH₂CH₂CH(CH₃)₂ |
| 222 | H | H | —CH₂CH(CH₃)₂ | —H | —CH₂CH₂CH(CH₃)₂ |
| 223 | Boc | H | —CH₂CH₂CH₂CH₃ | —H | —CH₂CH₂CH(CH₃)₂ |
| 224 | H | H | —CH₂CH₂CH₂CH₃ | —H | —CH₂CH₂CH(CH₃)₂ |
| 225 | Boc | H | —CH₂—C₆H₅ 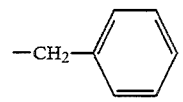 | —H | —CH₂CH₂CH(CH₃)₂ |
| 226 | H | H | —CH₂—C₆H₅ 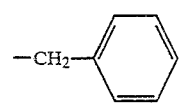 | —H | —CH₂CH₂CH(CH₃)₂ |
| 227 | Boc | H | —CH₂CH(CH₃)₂ | —H | 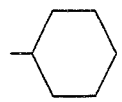 |

TABLE 2-continued

| Comp. No. | R¹ | R² | R⁵ | R⁶ | R⁹ |
|---|---|---|---|---|---|
| 228 | H | H | —CH₂CH(CH₃)₂ | —H | cyclohexyl |
| 229 | Boc | H | —CH₂CH₂CH₂CH₃ | —H | cyclohexyl |
| 230 | H | H | —CH₂CH₂CH₂CH₃ | —H | cyclohexyl |
| 231 | Boc | —H | —CH₂—C₆H₅ | —H | cyclohexyl |
| 232 | H | —H | —CH₂—C₆H₅ | —H | cyclohexyl |
| 233 | Boc | —H | —CH₂CH(CH₃)₂ | —H | —CH=CH₂ |
| 234 | H | —H | —CH₂CH(CH₃)₂ | —H | —CH=CH₂ |
| 235 | Boc | —H | —CH₂CH₂CH₂CH₃ | —H | —CH=CH₂ |
| 236 | H | —H | —CH₂CH₂CH₂CH₃ | —H | —CH=CH₂ |
| 237 | Boc | —H | —CH₂—C₆H₅ | —H | —CH=CH₂ |
| 238 | H | —H | —CH₂—C₆H₅ | —H | —CH=CH₂ |
| 239 | Boc | —H | —CH₂CH(CH₃)₂ | —H | trans-CH=CH-CH₂CH₂CH₂CH₃ |
| 240 | H | —H | —CH₂CH(CH₃)₂ | —H | trans-CH=CH-CH₂CH₂CH₂CH₃ |
| 241 | Boc | —H | —CH₂CH₂CH₂CH₃ | —H | trans-CH=CH-CH₂CH₂CH₂CH₃ |
| 242 | H | —H | —CH₂CH₂CH₂CH₃ | —H | trans-CH=CH-CH₂CH₂CH₂CH₃ |
| 243 | Boc | —H | —CH₂—C₆H₅ | —H | trans-CH=CH-CH₂CH₂CH₂CH₃ |
| 244 | H | —H | —CH₂—C₆H₅ | —H | trans-CH=CH-CH₂CH₂CH₂CH₃ |
| 245 | Boc | —H | —CH₂CH(CH₃)₂ | —H | cis-CH=CH-CH₂CH₂CH₂CH₃ |
| 246 | H | —H | —CH₂CH(CH₃)₂ | —H | cis-CH=CH-CH₂CH₂CH₂CH₃ |
| 247 | Boc | —H | —CH₂CH₂CH₂CH₃ | —H | cis-CH=CH-CH₂CH₂CH₂CH₃ |

TABLE 2-continued

| Comp. No. | R¹ | R² | R⁵ | R⁶ | R⁹ |
|---|---|---|---|---|---|
| 248 | H | —H | —CH$_2$CH$_2$CH$_2$CH$_3$ | —H | 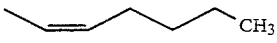 |
| 249 | Boc | —H | —CH$_2$—C$_6$H$_5$ | —H | 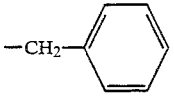 |
| 250 | H | —H | —CH$_2$—C$_6$H$_5$ | —H | 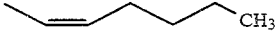 |
| 251 | Boc | —H | —CH$_2$CH(CH$_3$)$_2$ | —H | —CH$_2$CH=CH$_2$ |
| 252 | H | —H | —CH$_2$CH(CH$_3$)$_2$ | —H | —CH$_2$CH=CH$_2$ |
| 253 | Boc | —H | —CH$_2$CH$_2$CH$_2$CH$_3$ | —H | —CH$_2$CH=CH$_2$ |
| 254 | H | —H | —CH$_2$CH$_2$CH$_2$CH$_3$ | —H | —CH$_2$CH=CH$_2$ |
| 255 | Boc | —H | —CH$_2$—C$_6$H$_5$ | —H | —CH$_2$CH=CH$_2$ |
| 256 | H | —H | —CH$_2$—C$_6$H$_5$ | —H | —CH$_2$CH=CH$_2$ |
| 257 | Boc | —H | —H | —H | 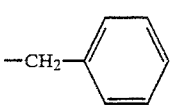 |
| 258 | H | —H | —H | —H | 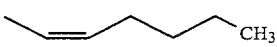 |
| 259 | Boc | —H | —CH$_3$ | —H | 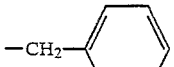 |
| 260 | H | —H | —CH$_3$ | —H | 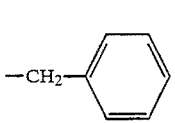 |
| 261 | Boc | —H | —CH(CH$_3$)$_2$ | —H | 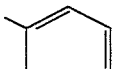 |
| 262 | H | —H | —CH(CH$_3$)$_2$ | —H | 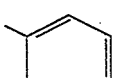 |
| 263 | Z | —H | —CH(CH$_3$)$_2$ | —H | 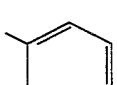 |
| 264 | pMZ | —H | —CH(CH$_3$)$_2$ | —H | 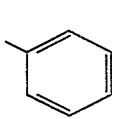 |

TABLE 2-continued
| Comp. No. | $R^1$ | $R^2$ | $R^5$ | $R^6$ | $R^9$ |
|---|---|---|---|---|---|
| 265 | Fmoc | —H | —CH(CH$_3$)$_2$ | —H | 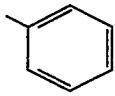 |
| 266 | Tos | —H | —CH(CH$_3$)$_2$ | —H | 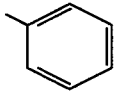 |
| 267 | Mts | —H | —CH(CH$_3$)$_2$ | —H | 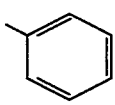 |
| 268 | Moc | —H | —CH(CH$_3$)$_2$ | —H | 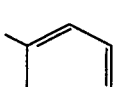 |
| 269 | Trt | —H | —CH(CH$_3$)$_2$ | —H | 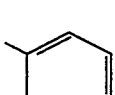 |
| 270 |  | Pht | —CH(CH$_3$)$_2$ | —H | 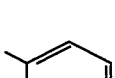 |
| 271 | Boc | —CH$_3$ | —CH(CH$_3$)$_2$ | —H | 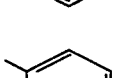 |
| 272 | H | —CH$_3$ | —CH(CH$_3$)$_2$ | —H | 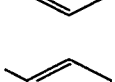 |
| 273 | Boc | —H | —CH$_2$CH(CH$_3$)$_2$ | —H | 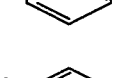 |
| 274 | H | —H | —CH$_2$CH(CH$_3$)$_2$ | —H | 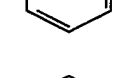 |
| 275 | Boc | —H | —CH$_2$CH$_2$CH$_2$CH$_3$ | —H | 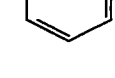 |
| 276 | H | —H | —CH$_2$CH$_2$CH$_2$CH$_3$ | —H | 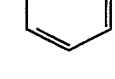 |
| 277 | Boc | —CH$_3$ | —CH$_2$CH$_2$CH$_2$CH$_3$ | —H | 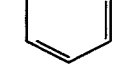 |

TABLE 2-continued
| Comp. No. | R¹ | R² | R⁵ | R⁶ | R⁹ |
|---|---|---|---|---|---|
| 278 | H | —CH₃ | —CH₂CH₂CH₂CH₃ | —H | 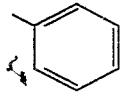 |
| 279 | Boc | —H | 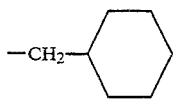 | —H | 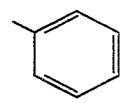 |
| 280 | H | —H | 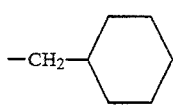 | —H | 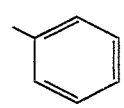 |
| 281 | Boc | —H | 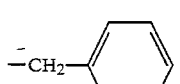 | —H | 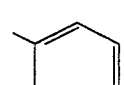 |
| 282 | H | —H | 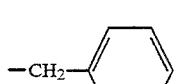 | —H | 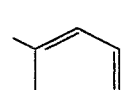 |
| 283 | Boc | —H | 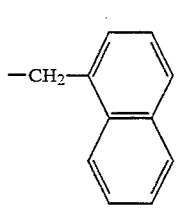 | —H | 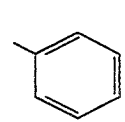 |
| 284 | H | —H | 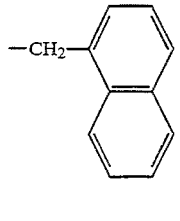 | —H | 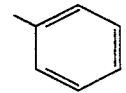 |
| 285 | Boc | —H | 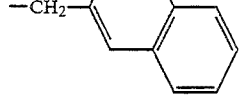 | —H | 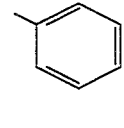 |
| 286 | H | —H | 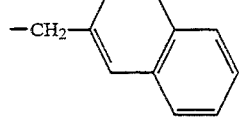 | —H | 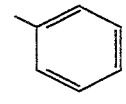 |
| 287 | Boc | —H | —CH₃ | —CH₃ | 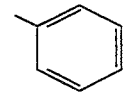 |
| 288 | H | —H | —CH₃ | —CH₃ | 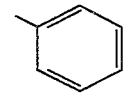 |

TABLE 2-continued
| Comp. No. | R¹ | R² | R⁵ | R⁶ | R⁹ |
|---|---|---|---|---|---|
| 289 | Boc | —H | —CH₂CH₃ | —CH₂CH₃ | 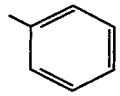 |
| 290 | H | —H | —CH₂CH₃ | —CH₂CH₃ | 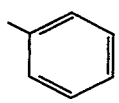 |
| 291 | Boc | —H | —CH₂CH₂CH₂CH₂— | | 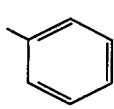 |
| 292 | H | —H | —CH₂CH₂CH₂CH₂— | | 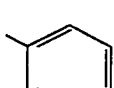 |
| 293 | Boc | —H | —CH₂CH₂CH₂CH₂CH₂— | | 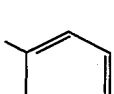 |
| 294 | H | —H | —CH₂CH₂CH₂CH₂CH₂— | | 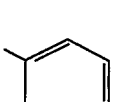 |
| 295 | Boc | —H | —CH(CH₃)₂ | —H | 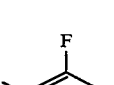 |
| 296 | H | —H | —CH(CH₃)₂ | —H | 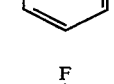 |
| 297 | Boc | —H | —CH₂CH₂CH₂CH₃ | —H | 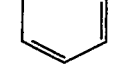 |
| 298 | H | —H | —CH₂CH₂CH₂CH₃ | —H | 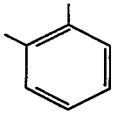 |
| 299 | Boc | —H | —CH(CH₃)₂ | —H | 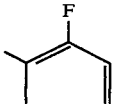 |
| 300 | H | —H | —CH(CH₃)₂ | —H | 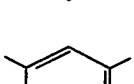 |

TABLE 2-continued
| Comp. No. | $R^1$ | $R^2$ | $R^5$ | $R^6$ | $R^9$ |
|---|---|---|---|---|---|
| 301 | Boc | —H | —CH$_2$CH$_2$CH$_2$CH$_3$ | —H | 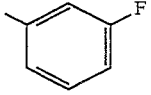 |
| 302 | H | —H | —CH$_2$CH$_2$CH$_2$CH$_3$ | —H | 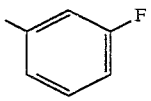 |
| 303 | Boc | —H | —CH(CH$_3$)$_2$ | —H | 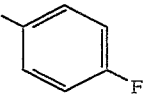 |
| 304 | H | —H | —CH(CH$_3$)$_2$ | —H | 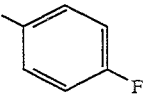 |
| 305 | Boc | —H | —CH$_2$CH$_2$CH$_2$CH$_3$ | —H | 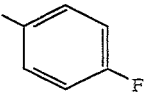 |
| 306 | H | —H | —CH$_2$CH$_2$CH$_2$CH$_3$ | —H | 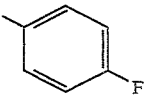 |
| 307 | Boc | —H | —CH(CH$_3$)$_2$ | —H | 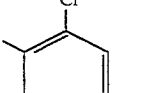 |
| 308 | H | —H | —CH(CH$_3$)$_2$ | —H | 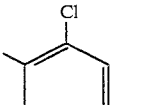 |
| 309 | Boc | —H | —CH$_2$CH$_2$CH$_2$CH$_3$ | —H | 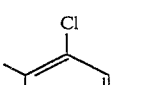 |
| 310 | H | —H | —CH$_2$CH$_2$CH$_2$CH$_3$ | —H | 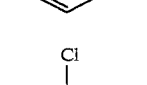 |
| 311 | Boc | —H | —CH(CH$_3$)$_2$ | —H | 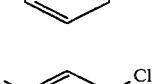 |
| 312 | H | —H | —CH(CH$_3$)$_2$ | —H | 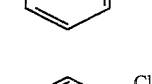 |

TABLE 2-continued
| Comp. No. | $R^1$ | $R^2$ | $R^5$ | $R^6$ | $R^9$ |
|---|---|---|---|---|---|
| 313 | Boc | —H | —CH₂CH₂CH₂CH₃ | —H | 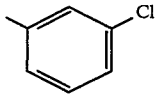 |
| 314 | H | —H | —CH₂CH₂CH₂CH₃ | —H | 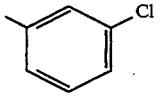 |
| 315 | Boc | —H | —CH(CH₃)₂ | —H | 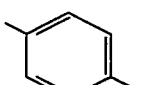 |
| 316 | H | —H | —CH(CH₃)₂ | —H | 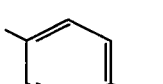 |
| 317 | Boc | —H | —CH₂CH₂CH₂CH₃ | —H | 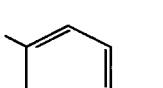 |
| 318 | H | —H | —CH₂CH₂CH₂CH₃ | —H | 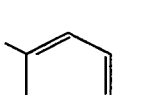 |
| 319 | Boc | —H | —CH(CH₃)₂ | —H | 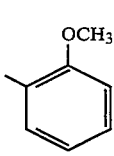 |
| 320 | H | —H | —CH(CH₃)₂ | —H | 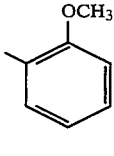 |
| 321 | Boc | —H | —CH₂CH₂CH₂CH₃ | —H | 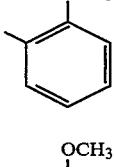 |
| 322 | H | —H | —CH₂CH₂CH₂CH₃ | —H | 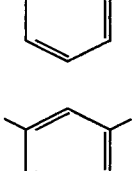 |
| 323 | Boc | —H | —CH(CH₃)₂ | —H | 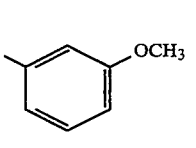 |
| 324 | H | —H | —CH(CH₃)₂ | —H |  |

TABLE 2-continued

| Comp. No. | $R^1$ | $R^2$ | $R^5$ | $R^6$ | $R^9$ |
|---|---|---|---|---|---|
| 325 | Boc | —H | —CH$_2$CH$_2$CH$_2$CH$_3$ | —H | 3-methoxyphenyl |
| 326 | H | —H | —CH$_2$CH$_2$CH$_2$CH$_3$ | —H | 3-methoxyphenyl |
| 327 | Boc | —H | —CH(CH$_3$)$_2$ | —H | 4-methoxyphenyl |
| 328 | H | —H | —CH(CH$_3$)$_2$ | —H | 4-methoxyphenyl |
| 329 | Boc | —H | —CH$_2$CH$_2$CH$_2$CH$_3$ | —H | 4-methoxyphenyl |
| 330 | H | —H | —CH$_2$CH$_2$CH$_2$CH$_3$ | —H | 4-methoxyphenyl |
| 331 | Boc | —H | —CH(CH$_3$)$_2$ | —H | 2-methylphenyl |
| 332 | H | —H | —CH(CH$_3$)$_2$ | —H | 2-methylphenyl |
| 333 | Boc | —H | —CH$_2$CH$_2$CH$_2$CH$_3$ | —H | 2-methylphenyl |
| 334 | H | —H | —CH$_2$CH$_2$CH$_2$CH$_3$ | —H | 2-methylphenyl |
| 335 | Boc | —H | —CH(CH$_3$)$_2$ | —H | 3-methylphenyl |
| 336 | H | —H | —CH(CH$_3$)$_2$ | —H | 3-methylphenyl |

TABLE 2-continued
| Comp. No. | R¹ | R² | R⁵ | R⁶ | R⁹ |
|---|---|---|---|---|---|
| 337 | Boc | —H | —CH₂CH₂CH₂CH₃ | —H | 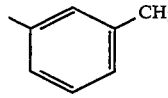 |
| 338 | H | —H | —CH₂CH₂CH₂CH₃ | —H | 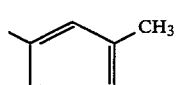 |
| 339 | Boc | —H | —CH(CH₃)₂ | —H | 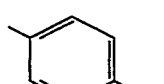 |
| 340 | H | —H | —CH(CH₃)₂ | —H | 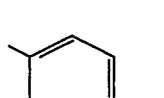 |
| 341 | Boc | —H | —CH₂CH₂CH₂CH₃ | —H | 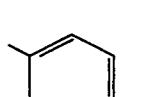 |
| 342 | H | —H | —CH₂CH₂CH₂CH₃ | —H | 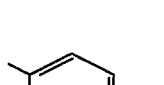 |
| 343 | Boc | —H | —CH₃ | —H | 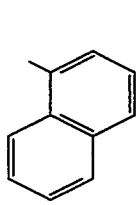 |
| 344 | H | —H | —CH₃ | —H | 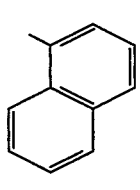 |
| 345 | Boc | —H | —CH(CH₃)₂ | —H | 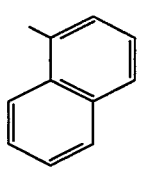 |
| 346 | H | —H | —CH(CH₃)₂ | —H | 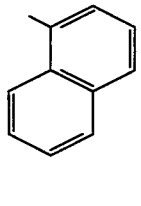 |

TABLE 2-continued
| Comp. No. | $R^1$ | $R^2$ | $R^5$ | $R^6$ | $R^9$ |
|---|---|---|---|---|---|
| 347 | Boc | —H | —CH$_2$CH(CH$_3$)$_2$ | —H | 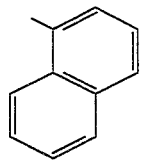 |
| 348 | H | —H | —CH$_2$CH(CH$_3$)$_2$ | —H | 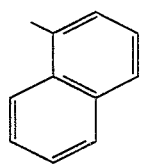 |
| 349 | Boc | —H | —CH$_2$CH$_2$CH$_2$CH$_3$ | —H | 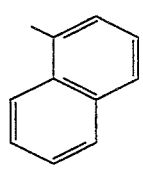 |
| 350 | H | —H | —CH$_2$CH$_2$CH$_2$CH$_3$ | —H | 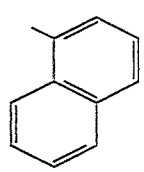 |
| 351 | Boc | —H | —CH$_3$ | —H | 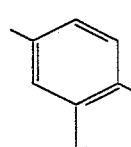 |
| 352 | H | —H | —CH$_3$ | —H | 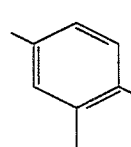 |
| 353 | Boc | —H | —CH(CH$_3$)$_2$ | —H | 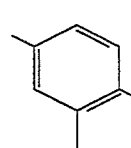 |
| 354 | H | —H | —CH(CH$_3$)$_2$ | —H | 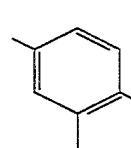 |
| 355 | Boc | —H | —CH$_2$CH(CH$_3$)$_2$ | —H | 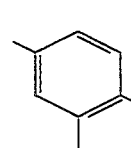 |

TABLE 2-continued
| Comp. No. | R¹ | R² | R⁵ | R⁶ | R⁹ |
|---|---|---|---|---|---|
| 356 | H | —H | —CH₂CH(CH₃)₂ | —H | 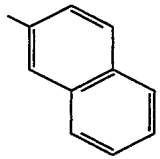 |
| 357 | Boc | —H | —CH₂CH₂CH₂CH₃ | —H | 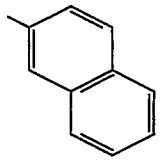 |
| 358 | H | —H | —CH₂CH₂CH₂CH₃ | —H | 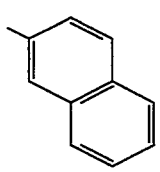 |
| 359 | Boc | —H | —CH(CH₃)₂ | —H | 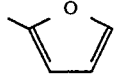 |
| 360 | H | —H | —CH(CH₃)₂ | —H | 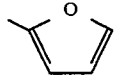 |
| 361 | Boc | —H | —CH₂CH₂CH₂CH₃ | —H | 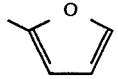 |
| 362 | H | —H | —CH₂CH₂CH₂CH₃ | —H | 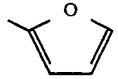 |
| 363 | Boc | —H | —CH(CH₃)₂ | —H | 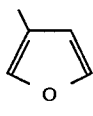 |
| 364 | H | —H | —CH(CH₃)₂ | —H | 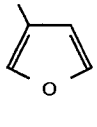 |
| 365 | Boc | —H | —CH₂CH₂CH₂CH₃ | —H | 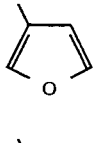 |
| 366 | H | —H | —CH₂CH₂CH₂CH₃ | —H |  |
| 367 | Boc | —H | —CH(CH₃)₂ | —H |  |

TABLE 2-continued
| Comp. No. | R¹ | R² | R⁵ | R⁶ | R⁹ |
|---|---|---|---|---|---|
| 368 | H | —H | —CH(CH₃)₂ | —H | 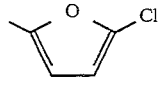 |
| 369 | Boc | —H | —CH₂CH₂CH₂CH₃ | —H |  |
| 370 | H | —H | —CH₂CH₂CH₂CH₃ | —H | 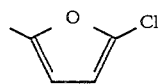 |
| 371 | Boc | —H | —CH(CH₃)₂ | —H | 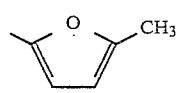 |
| 372 | H | —H | —CH(CH₃)₂ | —H | 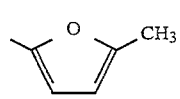 |
| 373 | Boc | —H | —CH₂CH₂CH₂CH₃ | —H | 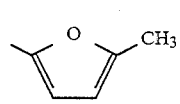 |
| 374 | H | —H | —CH₂CH₂CH₂CH₃ | —H | 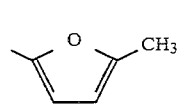 |
| 375 | Boc | —H | —CH(CH₃)₂ | —H | 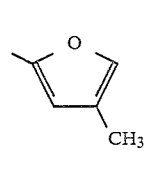 |
| 376 | H | —H | —CH(CH₃)₂ | —H | 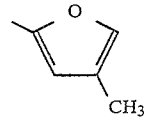 |
| 377 | Boc | —H | —CH₂CH₂CH₂CH₃ | —H | 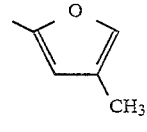 |
| 378 | H | —H | —CH₂CH₂CH₂CH₃ | —H | 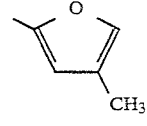 |
| 379 | Boc | —H | —CH(CH₃)₂ | —H | 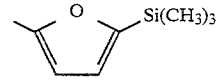 |
| 380 | H | —H | —CH(CH₃)₂ | —H | 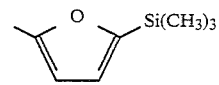 |
| 381 | Boc | —H | —CH₂CH(CH₃)₂ | —H | 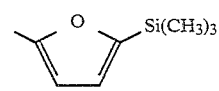 |

TABLE 2-continued
| Comp. No. | R¹ | R² | R⁵ | R⁶ | R⁹ |
|---|---|---|---|---|---|
| 382 | H | —H | —CH₂CH(CH₃)₂ | —H | 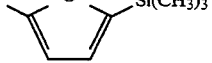 |
| 383 | Boc | —H | —CH₂CH₂CH₂CH₃ | —H | 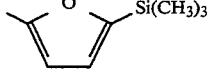 |
| 384 | H | —H | —CH₂CH₂CH₂CH₃ | —H |  |
| 385 | Boc | —H | —CH(CH₃)₂ | —H | 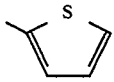 |
| 386 | H | —H | —CH(CH₃)₂ | —H | 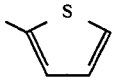 |
| 387 | Boc | —H | —CH₂CH₂CH₂CH₃ | —H | 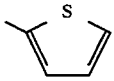 |
| 388 | H | —H | —CH₂CH₂CH₂CH₃ | —H | 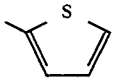 |
| 389 | Boc | —H | —CH(CH₃)₂ | —H | 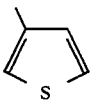 |
| 390 | H | —H | —CH(CH₃)₂ | —H | 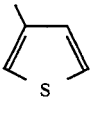 |
| 391 | Boc | —H | —CH₂CH₂CH₂CH₃ | —H | 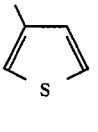 |
| 392 | H | —H | —CH₂CH₂CH₂CH₃ | —H | 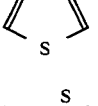 |
| 393 | Boc | —H | —CH(CH₃)₂ | —H | 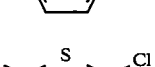 |
| 394 | H | —H | —CH(CH₃)₂ | —H | 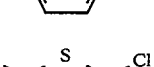 |
| 395 | Boc | —H | —CH₂CH₂CH₂CH₃ | —H | 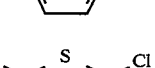 |
| 396 | H | —H | —CH₂CH₂CH₂CH₃ | —H | 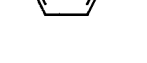 |

TABLE 2-continued

| Comp. No. | R¹ | R² | R⁵ | R⁶ | R⁹ |
|---|---|---|---|---|---|
| 397 | Boc | —H | —CH(CH₃)₂ | —H | 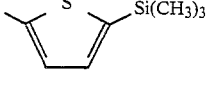 |
| 398 | H | —H | —CH(CH₃)₂ | —H | 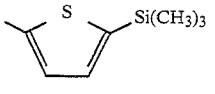 |
| 399 | Boc | —H | —CH₂CH(CH₃)₂ | —H | 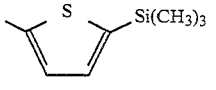 |
| 400 | H | —H | —CH₂CH(CH₃)₂ | —H | 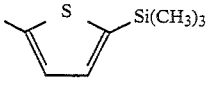 |
| 401 | Boc | —H | —CH₂CH₂CH₂CH₃ | —H | 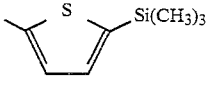 |
| 402 | H | —H | —CH₂CH₂CH₂CH₃ | —H | 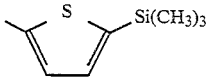 |
| 403 | Boc | —H | —CH(CH₃)₂ | —H | —CH₂OH |
| 404 | H | —H | —CH(CH₃)₂ | —H | —CH₂OH |
| 405 | Boc | —H | —CH₂CH₂CH₂CH₃ | —H | —CH₂OH |
| 406 | H | —H | —CH₂CH₂CH₂CH₃ | —H | —CH₂OH |
| 407 | Boc | —H | —CH(CH₃)₂ | —H | —CH(CH₃)OH |
| 408 | H | —H | —CH(CH₃)₂ | —H | —CH(CH₃)OH |
| 409 | Boc | —H | —CH₂CH(CH₃)₂ | —H | —CH(CH₃)OH |
| 410 | H | —H | —CH₂CH(CH₃)₂ | —H | —CH(CH₃)OH |
| 411 | Boc | —H | —CH(CH₃)₂ | —H | —CH(CH₂)₃CH₃<br>\|<br>OH |
| 412 | H | —H | —CH(CH₃)₂ | —H | —CH(CH₂)₃CH₃<br>\|<br>OH |
| 413 | Boc | —H | —CH₂CH₂CH₂CH₃ | —H | —CH(CH₂)₃CH₃<br>\|<br>OH |
| 414 | H | —H | —CH₂CH₂CH₂CH₃ | —H | —CH(CH₂)₃CH₃<br>\|<br>OH |
| 415 | Boc | —H | —CH₃ | —H | —C(CH₃)₂OH |
| 416 | H | —H | —CH₃ | —H | —C(CH₃)₂OH |
| 417 | Boc | —H | —CH(CH₃)₂ | —H | —C(CH₃)₂OH |
| 418 | H | —H | —CH(CH₃)₂ | —H | —C(CH₃)₂OH |
| 419 | Z | —H | —CH(CH₃)₂ | —H | —C(CH₃)₂OH |
| 420 | Fmoc | —H | —CH(CH₃)₂ | —H | —C(CH₃)₂OH |
| 421 | Boc | —H | —CH₂CH(CH₃)₂ | —H | —C(CH₃)₂OH |
| 422 | H | —H | —CH₂CH(CH₃)₂ | —H | —C(CH₃)₂OH |
| 423 | Boc | —H | CH₃<br>\|<br>—CHCH₂CH₃ | —H | —C(CH₃)₂OH |
| 424 | H | —H | CH₃<br>\|<br>—CHCH₂CH₃ | —H | —C(CH₃)₂OH |
| 425 | Boc | —H | —CH₂CH₂CH₂CH₃ | —H | —C(CH₃)₂OH |

TABLE 2-continued

| Comp. No. | R¹ | R² | R⁵ | R⁶ | R⁹ |
|---|---|---|---|---|---|
| 426 | H | —H | —CH₂CH₂CH₂CH₃ | —H | —C(CH₃)₂OH |
| 427 | Boc | —H | —CH₂-cyclohexyl | —H | —C(CH₃)₂OH |
| 428 | H | —H | —CH₂-cyclohexyl | —H | —C(CH₃)₂OH |
| 429 | Boc | —H | —CH₂-phenyl | —H | —C(CH₃)₂OH |
| 430 | H | —H | —CH₂-phenyl | —H | —C(CH₃)₂OH |
| 431 | Boc | —H | —CH₃ | —H | —CH(OH)-phenyl |
| 432 | H | —H | —CH₃ | —H | —CH(OH)-phenyl |
| 433 | Boc | —H | —CH(CH₃)₂ | —H | —CH(OH)-phenyl |
| 434 | H | —H | —CH(CH₃)₂ | —H | —CH(OH)-phenyl |
| 435 | Boc | —H | —CH₂CH(CH₃)₂ | —H | —CH(OH)-phenyl |
| 436 | H | —H | —CH₂CH(CH₃)₂ | —H | —CH(OH)-phenyl |
| 437 | Boc | —H | —CH₂CH₂CH₂CH₃ | —H | —CH(OH)-phenyl |
| 438 | H | —H | —CH₂CH₂CH₂CH₃ | —H | —CH(OH)-phenyl |
| 439 | Boc | —H | —CH(CH₃)₂ | —H | —C(CH₃)(OH)-phenyl |

TABLE 2-continued
| Comp. No. | $R^1$ | $R^2$ | $R^5$ | $R^6$ | $R^9$ |
|---|---|---|---|---|---|
| 440 | H | —H | —CH(CH$_3$)$_2$ | —H | 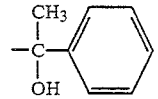 |
| 441 | Boc | —H | —CH$_2$CH$_2$CH$_2$CH$_3$ | —H | 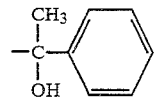 |
| 442 | H | —H | —CH$_2$CH$_2$CH$_2$CH$_3$ | —H | 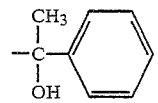 |

TABLE 3

| Comp. No. | $R^1$ | $R^2$ | $R^3$ | $R^4$ | $R^5$ | $R^6$ | $R^{10}$ | $R^{11}$ | $R^9$ |
|---|---|---|---|---|---|---|---|---|---|
| 443 | Boc | H | —CH₂CH(CH₃)₂ | H | —CH(CH₃)₂ | H | | —CH₂CCH₂— with CH₃, CH₃ | H |
| 444 | Boc | H | —CH₂CH(CH₃)₂ | H | —CH₂CH₂CH₂CH₃ | H | —CH₃ | | H |
| 445 | Boc | H | —CH₂CH(CH₃)₂ | H | —CH₂CH₂CH₂CH₃ | H | —CH₂CH₃ | | H |
| 446 | Boc | H | —CH₂CH(CH₃)₂ | H | —CH₂CH₂CH₂CH₃ | H | —CH₂—(phenyl) | | H |
| 447 | Boc | H | —CH₂CH(CH₃)₂ | H | —CH₂CH₂CH₂CH₃ | H | | —CH₂CH₂— | H |
| 448 | Boc | H | —CH₂CH(CH₃)₂ | H | —CH₂CH₂CH₂CH₃ | H | | —CH₂CH₂CH₂— | H |
| 449 | Boc | H | —CH₂CH(CH₃)₂ | H | —CH₂CH₂CH₂CH₃ | H | | —CH₂CCH₂— with CH₃, CH₃ | H |
| 450 | Z | H | —CH₂CH(CH₃)₂ | H | —CH₂CH₂CH₂CH₃ | H | | —CH₂CCH₂— with CH₃, CH₃ | H |
| 451 | Fmoc | H | —CH₂CH(CH₃)₂ | H | —CH₂CH₂CH₂CH₃ | H | | —CH₂CCH₂— with CH₃, CH₃ | H |
| 452 | Boc | H | —CH₂CH(CH₃)₂ | H | —CH₂CH₂CH₂CH₃ | H | | —CHCH₂CH— with CH₃, CH₃ | H |
| 453 | Boc | H | —CH₂—(cyclohexyl) | H | —CH₂CH₂CH₂CH₃ | H | | —CH₂CCH₂— with CH₃, CH₃ | H |
| 454 | Boc | H | —CH₂—(phenyl) | H | —CH₂CH₂CH₂CH₃ | H | | —CH₂CCH₂— with CH₃, CH₃ | H |

TABLE 3-continued

| Comp. No. | R¹ | R² | R³ | R⁴ | R⁵ | R⁶ | R¹⁰ | R¹¹ | R⁹ |
|---|---|---|---|---|---|---|---|---|---|
| 455 | Boc | H | —CH₃ | H | —CH₂—C₆H₅ | H | | CH₃—CH₂CH₂—CH₃ | H |
| 456 | Boc | H | —CH(CH₃)₂ | H | —CH₂—C₆H₅ | H | | CH₃—CH₂CH₂—CH₃ | H |
| 457 | Boc | H | —CH₂CH(CH₃)₂ | H | —CH₂—C₆H₅ | H | | CH₃—CH₂CH₂—CH₃ | H |
| 458 | Boc | H | —CH₂CH(CH₃)₂ | H | —CH₂CH₂CH₂CH₃ | H | | CH₃—CH₂CH₂—CH₃ | —CH₃ |
| 459 | Boc | H | —CH₂CH(CH₃)₂ | H | —CH₂CH₂CH₂CH₃ | H | | CH₃—CH₂CH₂—CH₃ | —CH=CH₂ |
| 460 | Boc | H | —CH₂—C₆H₅ | H | —CH₃ | H | | CH₃—CH₂CH₂—CH₃ | —C₆H₅ |
| 461 | Boc | H | —CH₃ | H | —CH(CH₃)₂ | H | | CH₃—CH₂CH₂—CH₃ | —C₆H₅ |
| 462 | Boc | H | —CH(CH₃)₂ | H | —CH(CH₃)₃ | H | | CH₃—CH₂CH₂—CH₃ | —C₆H₅ |
| 463 | Boc | H | —CH₂CH(CH₃)₂ | H | —CH(CH₃)₂ | H | —CH₃ | —CH₃ | —C₆H₅ |

TABLE 3-continued

| Comp. No. | $R^1$ | $R^2$ | $R^3$ | $R^4$ | $R^5$ | $R^6$ | $R^{10}$ | $R^{11}$ | $R^9$ |
|---|---|---|---|---|---|---|---|---|---|
| 464 | Boc | H | —CH$_2$CH(CH$_3$)$_2$ | H | —CH$_2$(CH$_3$)$_2$ | H | —CH$_2$CH$_3$ | —CH$_2$CH$_3$ |  |
| 465 | Boc | H | —CH$_2$CH(CH$_3$)$_2$ | H | —CH$_2$(CH$_3$)$_2$ | H |  —CH$_2$— | 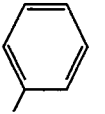 —CH$_2$— | 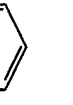 |
| 466 | Boc | H | —CH$_2$CH(CH$_3$)$_2$ | H | —CH(CH$_3$)$_2$ | H | | —CH$_2$CH$_2$— | 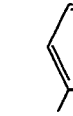 |
| 467 | Boc | H | —CH$_2$CH(CH$_3$)$_2$ | H | —CH(CH$_3$)$_2$ | H | | —CH$_2$CH$_2$CH$_2$— | 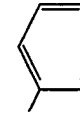 |
| 468 | Boc | H | —CH$_2$CH(CH$_3$)$_2$ | H | —CH(CH$_3$)$_2$ | H | | —CH$_2$CCH$_2$— with CH$_3$/CH$_3$ | 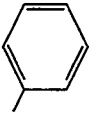 |
| 469 | Boc | H | —CH$_2$CH(CH$_3$)$_2$ | —CH$_3$ | —CH(CH$_3$)$_2$ | H | | —CH$_2$CCH$_2$— with CH$_3$/CH$_3$ |  |
| 470 | Boc | —CH$_3$ | —CH$_2$CH(CH$_3$)$_2$ | H | —CH(CH$_3$)$_2$ | H | | —CH$_2$CCH$_2$— with CH$_3$/CH$_3$ |  |
| 471 | Boc | —CH$_3$ | —CH$_2$CH(CH$_3$)$_2$ | —CH$_3$ | —CH(CH$_3$)$_2$ | H | | —CH$_2$CCH$_2$— with CH$_3$/CH$_3$ | 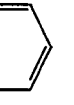 |

TABLE 3-continued

| Comp. No. | R¹ | R² | R³ | R⁴ | R⁵ | R⁶ R¹⁰ | R¹¹ | R⁹ |
|---|---|---|---|---|---|---|---|---|
| 472 | Z | H | —CH₂CH(CH₃)₂ | H | —CH(CH₃)₂ | H | —CH₂CCH₂— with CH₃, CH₃, CH₃ | phenyl |
| 473 | Fmoc | H | —CH₂CH(CH₃)₂ | H | —CH(CH₃)₂ | H | —CH₂CCH₂— with CH₃, CH₃, CH₃ | phenyl |
| 474 | Boc | H | —CH₂CH(CH₃)₂ | H | —CH(CH₃)₂ | H | —CHCH₂CH— with CH₃, CH₃, CH₃ | phenyl |
| 475 | Boc | H | —CH₂CH₂CH₂CH₃ | H | —CH(CH₃)₂ | H | —CH₂CCH₂— with CH₃, CH₃, CH₃ | phenyl |
| 476 | Boc | H | —CH₂-cyclohexyl | H | —CH(CH₃)₂ | H | —CH₂CCH₂— with CH₃, CH₃, CH₃ | phenyl |
| 477 | Boc | H | —CH₂-phenyl | H | —CH(CH₃)₂ | H | —CH₂CCH₂— with CH₃, CH₃, CH₃ | phenyl |
| 478 | Boc | H | —CH₂CH(CH₃)₂ | H | —CH(CH₃)₂ | H | —CH₂CCH₂— with CH₃, CH₃, CH₃ | phenyl |
| 479 | Boc | H | —CH₂CH(CH₃)₂ | H | —CH₂CH₂CH₂CH₃ | H | —CH₂CCH₂— with CH₃, CH₃, CH₃ | phenyl |

TABLE 3-continued

| Comp. No. | R¹ | R² | R³ | R⁴ | R⁵ | R⁶ | R¹⁰ | R¹¹ | R⁹ |
|---|---|---|---|---|---|---|---|---|---|
| 480 | Z | H | —CH₂CH(CH₃)₂ | H | —CH₂CH₂CH₂CH₃ | H | | —CH₂CCH₂— with CH₃ and CH₃ | 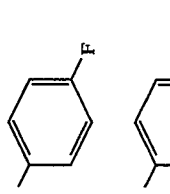 |
| 481 | Boc | H | —CH(CH₃)₂ | H | —CH₂— cyclohexyl | H | | —CH₂CCH₂— with CH₃ and CH₃ | 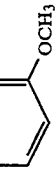 |
| 482 | Boc | H | —CH₂CH(CH₃)₂ | H | —CH₂— cyclohexyl | H | | —CH₂CCH₂— with CH₃ and CH₃ | 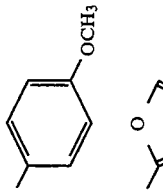 |
| 483 | Boc | H | —CH₂CH(CH₃)₂ | H | —CH₂CH₂CH₂CH₃ | H | | —CH₂CCH₂— with CH₃ and CH₃ | 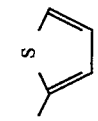 |
| 484 | Boc | H | —CH₂CH(CH₃)₂ | H | —CH₂CH₂CH₂CH₃ | H | | —CH₂CCH₂— with CH₃ and CH₃ |  |
| 485 | Boc | H | —CH₂CH(CH₃)₂ | H | —CH(CH₃)₂ | H | | —CH₂CCH₂— with CH₃ and CH₃ | —C(CH₃)(CH₂CH₃)OH |
| 486 | Boc | H | —CH₂CH(CH₃)₂ | H | —CH₂CH₂CH₂CH₃ | H | | —CH₂CCH₂— with CH₃ and CH₃ | —C(CH₃)(CH₂CH₃)OH |
| 487 | Boc | H | —CH₂CH(CH₃)₂ | H | —CH₂— phenyl | H | | —CH₂CCH₂— with CH₃ and CH₃ | —C(CH₃)(CH₂CH₃)OH |
| 488 | Boc | H | —CH₂CH(CH₃)₂ | H | —CH(CH₃)₂ | H | | —CH₂CCH₂— with CH₃ and CH₃ | 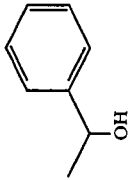 |

The process for the production of the compounds of the present invention will now be explained. The cyclopropene derivatives of the present invention may be produced, for example, by the following process:

Process 1: A process for producing a compound represented by the above general formula (I) wherein $R^7$ and $R^8$ represent $-OR^{10}$ and $-OR^{11}$, respectively:

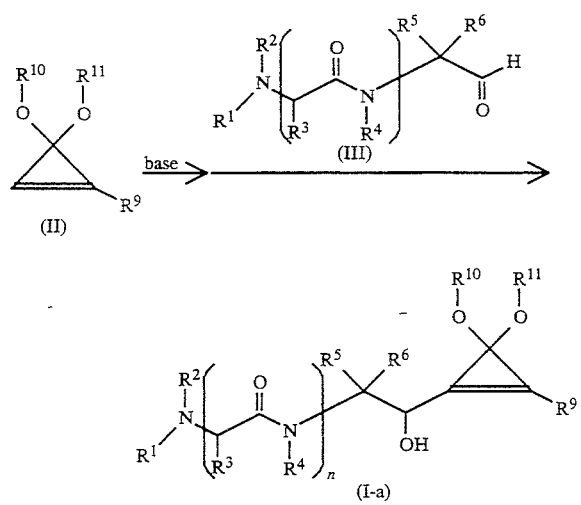

(In the above general formula, $R^1$, $R^2$, $R^3$, $R^4$, $R^5$, $R^6$, $R^9$, $R^{10}$, $R^{11}$ and n are those as defined above.)

Using the known process described in the reference (Tetrahedron Letters, Vol.32, pp.1339, 1991), cyclopropenone ketal derivative represented by the above general formula (II) is readily synthesized. The derivative is dissolved in an ethereal solvent such as tetrahydrofuran, diethylether, etc., followed by addition of a strong base such as n-butyl lithium, methyl lithium, lithium diisopropylamide in the presence of an additive such as tetramethylethylenediamine, hexamethylphosphoric triamide, 1,3-dimethyl-2-imidazolidone, etc. to prepare a lithiated compound thereof. Then, an aldehyde derivative represented by the above general formula (III) is added to the resulting lithiated compound to prepare the cyclopropene derivative represented by the above general formula (1-a). In the reaction, anhydrous cerium chloride suspension in a solvent such as tetrahydrofuran, diethylether, hexane and the like may further be added to the lithiated compound of the resulting compound (II) to transform the compound into the cerium salt thereof, with which the aldehyde derivative represented by the general formula (III) may be reacted.

Process 2: A process for producing a compound represented by the above general formula (I) wherein $R^7$, taken together with $R^8$ represents =O, and n is zero:

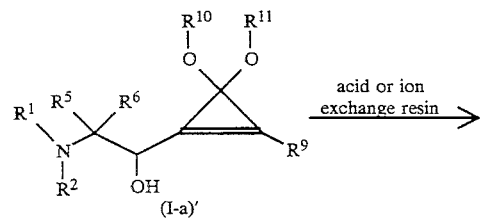

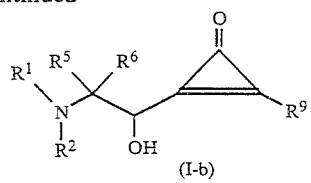

(In the above general formula, $R^1$, $R^2$, $R^5$, $R^6$, $R^9$, $R^{10}$, and $R^{11}$ are those as defined above.)

The cyclopropene derivative represented by the above general formula (I-a)', produced by the process of Process 1, is dissolved in acetone, diethyl ether, tetrahydrofuran, etc., followed by treatment with an ion exchange resin such as Amberlist 15 (registered trade mark) or followed by addition of a mineral acid such as dilute sulfuric acid to effect selective deprotection of ketal, whereby the cyclopropene derivative represented by the above general formula (I-b) is produced.

By the process described in Japanese Patent Application No. Hei 4-146024, the cyclopropene derivative represented by the above general formula (I) can be lead to cyclopropenone derivatives exhibiting a strong inhibitory activity against thiol protease such as calpain, papain, cathepsin B, cathepsin H, cathepsin L and the like.

The present invention will now be described in examples hereinbelow, but the invention is not limited to the examples, unless departing from the spirit and scope of the invention.

EXAMPLE 1

Preparation of
2-((2S)-2-tert-butoxycarbonylamino-1-hydroxy-3-methylbutyl)-3-phenylcyclopropenone
2,2-dimethyl-1,3-propanediyl acetal (Compound No. 65 in Table 1)

To a solution of 3.51 g of 2-phenylcyclopropenone 2,2-dimethyl-1,3-propanediyl acetal in 30 ml of tetrahydrofuran was added 3.8 g of N, N, N', N'-tetramethylethylenediamine. To the reaction solution chilled at −78° C. was added a 1.55 ml/l solution of n-butyl lithium in 10.5 ml of hexane, and the mixture was stirred for 20 minutes. Then, 30 ml of tetrahydrofuran suspension of anhydrous cerium chloride prepared by drying 8.0 g of cerium chloride heptahydrate at 140° C./1 mmHg for 2 hours was added to the mixture, which was stirred for 20 minutes. A solution of 1.82 g of N-tert-butoxycarbonyl-L-valinal in 20 ml of tetrahydrofuran was added, and the resultant mixture was stirred at −78° C. for 2 hours. A solution of 1 ml of water in 5 ml of tetrahydrofuran was added to the reaction mixture, which was allowed to warm at room temperature and filtered through celite. The celite was washed well with ethyl acetate, and the filtrate was dried over sodium sulfate, filtered, concentrated and chromatographed on a column of silica gel, eluting with hexane containing 20% ethyl acetate as a developing solvent to give 2.71 g of the titled product.

Yield: 72% IR (KBr, cm$^{-1}$): 3430, 2960, 1855, 1800, 1710, 1690 NMR (CD$_3$OD, δ): 0.95–1.60 (m, 12H), 1.38 (s, 3H), 1.42 (s, 6H), 1.95–2.15 (m, 1H), 3.60–3.75 (m, 1H), 3.75–3.95 (m, 4H), 5.0–5.10 (m, 1H), 6.03 (d, J=10 Hz, 0.33H), 6.23 (d, J=10 Hz, 0.67H), 7.40–7.65 (m, 3H), 7.70–7.90 (m, 2H)

In the same manner as in Example 1, the following compounds were produced.

EXAMPLE 2

Preparation of 2-(2-tert-butoxycarbonylamino-1-hydroxyethyl)cyclopropenone 2,2-dimethyl-l,3-propanediyl acetal (Compound No. 1 in Table 1)

NMR (CDCl$_3$, δ): 0.97 (s, 3H), 1.09 (s, 3H), 1.44 (s, 9H), 3.35–3.60 (m, 2B), 3.63 (s, 4H), 4.80–4.88 (m, 1H), 5.07–5.26 (m, 1H), 5.26–5.52 (m, 1H), 7.63 (s, 1H)

EXAMPLE 3

Preparation of 2-((2S)-2-tert-butoxycarbonylamino-1-hydroxy-3-methylbutyl)cyclopropenone 2,2-dimethyl-1-1,3-propanediyl acetal (Compound No. 3 in Table 1)

IR (neat, cm$^{-1}$): 3380, 1722, 1708, 1690 NMR (CDCl$_3$, δ): 0.87–1.10 (m, 12H), 1.43 (s, 7.2H), 1.45 (s, 1.8H), 2.05–2.20 (m, 1H), 3.35–3.70 (m, 5H), 4.80–5.03 (m, 2H), 7.57 (s, 0.8H), 7.71 (s, 0.2H)

EXAMPLE 4

Preparation of 2-((2S)-2-tert-butoxycarbonylamino-1-hydroxy-4-methylpentyl)cyclopropenone 2,2-dimethyl-1,3-propanediyl acetal (Compound No. 6 in Table 1)

IR (neat, cm$^{-1}$): 3445, 3360, 1705 NMR (CDCl$_3$, δ): 0.80–0.95 (m, 9H), 1.15 is, 3B), 1.44 (s, 9H), 1.55–1.78 (m, 3H), 3.63 (s, 2H), 3.65 (s, 2H), 3.72–3.95 (m, 1H), 4.70–4.84 (m, 2H), 5.02–5.15 (m, 1H), 7.68 (s, 0.9H), 7.71 (s, 0.1H)

EXAMPLE 5

Preparation of 2-((2S)-2-tert-butoxycarbonylamino-1-hydroxyhexyl)-cyclopropenone 2,2-dimethyl-1,3-propanediyl acetal (Compound No. 14 in Table 1)

IR (neat, cm$^{-1}$): 3460, 3370, 1700 NMR (CDCl$_3$, δ): 0.85–1.0 (m, 3H), 0.92 (s, 3H), 1.14 (s, 3H), 1.25–1.55 (m, 6H), 1.44 (s, 9H), 3.05–3.15 (m, 0.7H), 3.25–3.35 (m, 0.3H), 3.61 (s, 2H), 3.63 (s, 2H), 3.65–3.85 (m, 0.7H), 3.85–4.05 (m, 0.3H), 4.70–4.85 (m, 1H), 4.85–4.95 (m, 0.3H), 5.0–5.15 (m, 0.7H), 7.65 (s, 0.7H), 7.72 (s, 0.3H)

EXAMPLE 6

Preparation of 2-((2S)-2-benzyloxycarbonylamino-1-hydroxyhexyl)cyclopropenone 2,2-dimethyl-1,3-propanediyl acetal (Compound No. 16 in Table 1)

IR (neat, cm$^{-1}$): 3360, 1723 NMR (CDCl$_3$, δ): 0.75–0.98 (m, 6H), 1.08 (s, 1.5H), 1.12 (s, 1.5H), 1.18–1.60 (m, 6H), 3.04 (s, 0.5H), 3.32 (d, J=7.8 Hz, 0.5H), 3.55–3.70 (m, 4H), 3.80 (m, 0.5H), 4.01 (m, 0.5H), 4.76 (d, J=7.8 Hz, 0.5H), 4.83 (m, 0.5H), 5.11 (s, 2H), 5.13 (m, 0.5H), 5.63 (d, J=8.1 Hz, 0.5H), 7.65 (s, 0.5H), 7.73 (s, 0.5H)

EXAMPLE 7

Preparation of 2-((2S)-2-tert-butoxycarbonylamino-1-hydroxyhexyl)-3-methylcyclopropenone 2,2-dimethyl-1,3-propanediyl acetal (Compound No. 32 in Table 1)

NMR (CDCl$_3$, δ): 0.84–0.96 (m, 3H), 0.95 (s, 3H), 1.08 (s, 3H), 1.28–1.55 (m, 6H), 1.43 (s, 9H), 2.17 (s, 3H), 3.53–3.80 (m, 5H), 4.63–4.74 (m, 1H), 4.88–5.07 (m, 1H)

EXAMPLE 8

Preparation of 2-((2S)-2-tert-butoxycarbonylamino-1-hydroxy-4-methylpentyl)-3-ethylcyclopropenone 2,2-dimethyl-1,3-propanediyl acetal (Compound No. 34 in Table 1)

IR (neat, cm$^{-1}$): 3360, 1853, 1696, 1623 NMR (CDCl$_3$, δ): 0.88–1.01 (m, 12H), 1.32 (t, J=7.7 Hz, 3H), 1.37–1.55 (m, 2H), 1.41 (s, 9H), 1.60–1.78 (m, 1H), 2.69 (q, J=7.7 Hz, 2H), 3.55–3.70 (m, 4H), 3.79–4.02 (m, 1H), 4.67–4.78 (m, 1H), 4.80–5.03 (m, 1H), 5.16 –5.22 (m, 1H)

EXAMPLE 9

Preparation of 2-((2S)-2-tert-butoxycarbonylamino-1-hydroxyhexyl)-3-isopentylcyclopropenone 2,2-dimethyl-1,3-propanediyl acetal (Compound No. 41 in Table 1)

IR (neat, cm$^{-1}$): 3360, 1816,,1715, 1698 NMR (CDCl$_3$, δ): 0.78–0.98 (m, 12H), 1.11 (s, 3H), 1.18–1.77 (m, 9H), 1.43 (s, 9H), 2.53 (d, J=7.6 Hz, 2H), 3.56–3.80 (m, 5H), 4.65–4.80 (m, 1H), 4.98–5.12 (m, 1H)

EXAMPLE 10

Preparation of 2-((1S, 2S)-2-tert-butoxycarbonylamino-1-hydroxyhexyl)-3-((Z)-1-hexenyl)cyclopropenone 2,2-dimethyl-1,3-propanediyl acetal (Compound No. 53 in Table 1)

IR (neat, cm$^{-1}$): 3440, 1785, 1703 NMR (CDCl$_3$, δ): 0.80–0.97 (m, 9H), 1.19 (s, 3H), 1.21–1.80 (m, 10H), 1.43 (s, 9H), 2.35–2.50 (m, 2H), 2.82 (s, 1H), 3.57–3.82 (m, 5H), 4.66–4.85 (m, 2H), 5.82–6.06 (m, 2H)

EXAMPLE 11

Preparation of 2-[(2S)-2-(N-tert-butoxycarbonyl)methylamino-1-hydroxy-3-methylbutyl]-3-phenylcycloprene 2,2-dimethyl-1,3-propanediyl acetal (Compound No. 74 in Table 1)

IR (KBr, cm$^{-1}$): 3430, 1798, 1688, 1672 NMR (CD$_3$OD, δ): 0.80–1.35 (m, 12H), 1.45 (s, 9H), 2.30 (m, 1H), 2.69 (s, 1.5H), 2.72 (s, 1.5H), 3.65–3.90 (m, 4H), 4.09 (m, 1H), 5.02 (m, 1H), 7.30–7.52 (m, 3H), 7.70–7.82 (m, 2H)

EXAMPLE 12

Preparation of 2-((2S)-2-tert-butoxycarbonylamino-1-hydroxyhexyl)-3-phenylcyclopropenone 2,2-dimethyl-1,3-propanediyl acetal (Compound No. 76 in Table 1)

IR (KBr, cm$^{-1}$): 3310, 1800, 1720, 1792 NMR (CDCl$_3$, δ): 0.80–0.98 (m, 3H), 0.99 (s, 3H), 1.21 (s, 3H), 1.15–1.90 (m, 6H), 1.39 (s, 2.7H), 1.43 (s, 6.3H), 3.58 (m, 0.7H), 3.68–4.95 (m, 4.6H), 4.95–4.10 (m, 0.7H), 4.88–5.07 (m, 1.3H), 5.24 (d, J=7.4 Hz, 0.7H), 7.28–7.45 (m, 3H), 7.69 (d, J=6.5 Hz, 2H)

EXAMPLE 13

Preparation of 2-(2-tert-butoxycarbonylamino-1-hydroxy-2-methylpropyl)-3-phenylcyclopropenone 2,2-dimethyl-1,3-propanediyl acetal (Compound No. 82 in Table 1)

IR (KBr, cm$^{-1}$): 3290, 1800, 1673 NMR (CDCl$_3$, δ): 0.94 (s, 3H), 1.25 (s, 3H), 1.27 (s, 9H), 1.41 (s, 3H), 1.64 (s, 3H), 3.70–3.90 (m, 4H), 4.77 (d, J=8.6 Hz, 1H), 4.93 (s, 1H), 5.57 (s, 1H), 7.28–7.46 (m, 3H), 7.75 (dd, J=8.2 Hz, 1.4 Hz, 2H)

EXAMPLE 14

Preparation of 2-((2S)-2-tert-butoxycarbonylamino-1-hydroxy-3-methylbutyl)-3-(4-fluorophenyl) cyclopropenone 2,2-dimethyl-1,3-propanediyl acetal (Compound No. 90 in Table 1)

IR (KBr, cm$^{-1}$): 3340, 1802, 1710, 1695, 1602 NMR (CD$_3$OD, δ): 0.90–1.25 (m, 12H), 1.38 (s, 6.3H), 1.42 (s, 2.7H), 2.08 (m, 1H), 3.63 (m, 1H), 3.70–3.93 (m, 4H), 5.08 (d, J=4.5 Hz, 0.3H), 5.02 (d, J=4.5 Hz, 0.7H), 6.05 (d, J=10 Hz, 0.3H), 6.19 (d, J=10 Hz, 0.7H), 7.18–7.30 (m, 2H), 7.70–7.88 (m, 2H)

EXAMPLE 15

Preparation of 2-((2S)-2-tert-butoxycarbonylamino-1-hydroxyhexyl)-3-(2-tolyl)cyclopropenone 2,2-dimethyl-1,3propanediyl acetal (Compound No. 105 in Table 1)

NMR (CDCl$_3$, δ): 0.83–1.03 (m, 3H), 0.96 (s, 3H), 1.25 (s, 3H), 1.25–1.51 (m, 4H), 1.40 (s, 1.8H), 1.43 (s, 7.2H), 1.60–1.95 (m, 2H), 2.45 (s, 0.6H), 2.52 (s, 2.4H), 3.65–3.90 (m, 1H), 3.73 (s, 4H), 4.80–5.20 (m, 2H), 7.05–7.30 (m, 3H), 7.55–7.65 (m, 1H)

EXAMPLE 16

Preparation of 2-((2S)-2-tert-butoxycarbonylamino-1-hydroxyhexyl)-3-(5-trimethylsilyl-2-furyl)cyclopenone 2,2dimethyl-1,3-propandiyl acetal (Compound No. 130 in Table 1)

NMR (CDCl$_3$, δ): 0.28 (s, 9H), 0.85–0.95 (m, 6H), 1.22 (s, 3H), 1.21–1.85 (m, 15H), 3.65–4.05 (m, 5H), 4.80–5.20 (m, 3H), 6.70 (d, J=3.9 Hz, 1), 6.78 (d, J=3.9 Hz, 1H)

EXAMPLE 17

Preparation of 2-((2S)-2-tert-butoxycarbonylamino-1-hydroxyhexyl)-3-(5-trimethylsilyl-2-thienyl)cyclopropenone 2,2dimethyl-1,3-propanediyl acetal (Compound No. 139 in Table 1)

NMR (CDCl$_3$, δ): 0.34 (s, 9H), 0.84–0.97 (m, 6H), 1.24 (s, 3H), 1.27–1.50 (m, 13H), 1.55–1.92 (m, 2H), 3.64–4.04 (m, 5H), 4.83–5.30 (m, 2H), 7.21 (d, J=3.4 Hz, 1H), 7.38 (d, J=3.4 Hz, 1H)

EXAMPLE 18

Preparation of 2-((2S)-2-tert-butoxycarbonylamino-1-hydroxy-3-methylbutyl)-3-(1-hydroxy-1-methylbutyl)-3-(hydroxy-1-methylethyl)cyclopropenone 2,2-dimethyl-1,3-propanediyl acetal (Compound No. 147 in Table 1)

NMR (CDCl$_3$, δ): 0.92–1.07 (m, 12H), 1.41–1.53 (m, 15H), 1.80–2.05 (m, 1H), 3.56–3.78 (m, 5H), 4.84–4.90 (m, 1H), 5.10 (d, J=11 Hz, 0.3H), 5.26 (d, J=11 Hz, 0.7H), 6.0 (s, 2H)

EXAMPLE 19

Preparation of 2-((2S)-2-tert-butoxycarbonylamino-1-hydroxy-3-methylbutyl)-3-[(hydroxy)(phenyl)methyl]cyclopropenone 2,2-dimethyl-1,3-propanediyl acetal (Compound No. 156 in Table 1)

NMR (CDCl$_3$, δ): 0.86–1.12 (m, 12H), 1.36–1.48 (m, 9H), 1.77–2.05 (m, 1H), 3.40–3.78 (m, 5H), 4.82–4.92 (m, 1H), 5.24–5.42 (m, 1H), 5.67–5.74 (m, 2H), 5.98 (s, 1H), 7.25–7.50 (m, 5H)

EXAMPLE 20

Preparation of 2-((2S)-2-methoxycarbonylamino-3-methyl1-hydroxybutyl)-3-phenylcyclopropenone 2,2-dimethyl-1,3-diyl acetal (Compound No. 161 in Table 1)

IR (KBr, cm$^{-1}$): 3436, 3378, 1858, 1792, 1703, 1626 NMR (CD$_3$OD, δ): 0.88–1.35 (m, 12H), 1.90–2.15 (m, 1H), 3.55–3.90 (m, 8H), 4.95 (d, J=5.2 Hz, 0.2H), 4.98 (d, J=5.0 Hz, 0.8H), 7.32–7.55 (m, 3H), 7.60–7.83 (m, 2H)

EXAMPLE 21

Preparation of 2-[(2S)-2-((2S)-2-benzyloxycarbonylamino-3-methylvalerylamino)-1-hydroxyhexyl)-3-(4-fluorophenyl)cyclopropenone 2,2-dimethyl-1,3-propanediyl acetal (Compound No. 490 in Table 3)

IR (KBr, cm$^{-1}$): 3320, 1802, 1710, 1660, 1602 NMR (CD$_3$OD, δ): 0.70–1.18 (m, 15H), 1.18–1.95 (m, 9H), 3.66–3.90 (m, 4H), 4.02–4.30 (m, 2H), 4.95 (m, 1H), 5.02 (s, 2H), 7.10–7.40 (m, 7H), 7.40–7.60 (m, 1H), 7.70–7.83 (m, 2H)

EXAMPLE 22

Preparation of 2-((2S)-2-tert-butoxycarbonylamino-1-hydroxyhexyl) cyclopropenone (Compound No. 178 in Table 2)

To a solution of 8.80 g of 2-((2S)-2-tert-Butoxycarbonylamino-1-hydroxyhexyl) cyclopropenone 2,2-dimethyl-1.3-propanediyl acetal obtained in Example 5 in 100 ml of diethyl ether and 20 ml of tetrahydrofuran were added 0.2 ml of 2 N sulfuric acid and 1 ml of water, and the mixture was stirred for 30 minutes. After subsequent addition of 300 ml of ether, the resulting product was washed sequentially in 50 ml of an aqueous 0.01 N sodium hydroxide solution and an aqueous saturated brine. After drying over magnesium sulfate, the product was filtered and concentrated, followed by purification by silica gel column chromatography (eluent; hexane: ethyl acetate =1:2) to produce the objective product (3.15 g).

Yield: 47% IR (neat, cm$^{-1}$): 3440, 1835, 1700 NMR (CDCl$_3$, δ): 0.85–1.9 (m, 3H), 1.25–1.85 (m, 6H), 1.42 (s, 9H), 2.60–2.90 (m, 1H), 3.75–3.95 (m, 1H), 4.75–4.85 (m, 0.8H), 4.85–4.95 (m, 0.2H), 5.19 (d, J=9 Hz, 1H), 8.59 (s, 0.8H), 8.65 (s, 0.2H)

In the same manner as in Example 22, the following compounds were produced.

EXAMPLE 23

Preparation of
2-(2-tert-Butoxycarbonylamino-1-hydroxyethyl) cyclopropenone (Compound No. 163 in Table 2)

IR (neat, cm$^{-1}$): 3350, 1840, 1718, 1700 NMR (CDCl$_3$, δ): 1.44 (s, 9H), 3.43–3.70 (m, 2H), 4.84–4.97 (m, 2H), 5.15–5.70 (m, 1H), 8.63 (s, 1H)

EXAMPLE 24

Preparation of
2-((2S)-2-tert-Butoxycarbonylamino-1-hydroxy-3-methylbutyl) cyclopropenone (Compound No. 167 in Table 2)

IR (KBr, cm$^{-1}$): 3330, 1838, 1820, 1712, 1690, 1678 NMR (CDCl$_3$, δ): 1.02 (d, J=7.2 Hz, 2.1H), 1.05 (d, J=7.3 Hz, 2.1H), 1.08 (d, J=7.3 Hz, 0.9H), 1.11 (d, J=7.3 Hz, 0.9H), 1.41 (s, 6.3H), 1.43 (s, 2.7H), 1.90–2.05 (m, 0.3H), 2.15–2.33 (m, 0.7), 3.40 (m. 0.7H), 3.68 (m, 0.3H), 4.87–4.98 (m, 1H), 5.02–5.16 (m, 2H), 8.57 (s, 0.7H), 8.66 (s, 0.3H)

EXAMPLE 25

Preparation of 2-((2S)-2-tert-Butoxycarbonylamino-1-hydroxy-4-methylpentyl)cyclopropenone (Compound No. 172 in Table 2 )

IR (neat, cm$^{-1}$): 3350, 1833, 1700 NMR (CDCl$_3$, δ): 0.86–0.98 (m, 6H), 1.43 (s, 9H), 1.55–1.83 (m, 3H), 3.88–4.06 (m, 1H), 4.70–4.86 (m, 1H), 5.12–5.38 (m, 1H), 8.61 (s, 0.75H), 8.66 (s, 0.25H)

EXAMPLE 26

Preparation of
2-((2S)-2-benzyloxycarbonylamino-1hydroxyhexyl) cyclopropenone (Compound No. 190 in Table 2)

IR (neat, cm$^{-1}$): 3440, 3350, 1840, 1715 NMR (CDCl$_3$, δ): 0.82–0.98 (m, 3H), 1.26–1.80 (m, 6H), 3.85–4.05 (m, 1H), 4.76–4.84 (m, 1H), 4.86–4.93 (m, 0.4H), 5.02–5.16 (m, 2.6H), 5.27 (d, J=7.8 Hz, 0.4H), 5.47 (d, J=7.7 Hz, 0.6H), 8.44 (s, 0.4H), 8.49 (s, 0.6H)

EXAMPLE 27

Preparation of
2-((2S)-2-tert-Butoxycarbonylamino-1-hydroxy-3-phenylpropyl)cyclopropenone (Compound No. 199 in Table 2)

IR (KBr, cm$^{-1}$): 3265, 1838, 1700 NMR (CDCl$_3$, δ): 1.41 (s, 6.3H), 1.43 (s, 2.7H), 2.80–3.18 (m, 2H), 3.94–4.25 (m, 1H), 4.65–4.77 (m, 1H), 4.82–4.95 (m, 0.3H), 5.15–5.25 (m, 0.7H), 5.30–5.42 (m, 0.7H), 5.50–5.60 (m, 0.3H), 7.13–7.35 (m, 5H), 8.43 (s, 0.7H), 8.51 (s, 0.3H)

EXAMPLE 28

Preparation of
2-((2S)-2-tert-Butoxycarbonylamino-1-hydroxyhexyl)-3-methylcyclopropenone (Compound No. 215 in Table 2)

NMR (CDCl$_3$, δ): 0.87–0.96 (m, 3H), 1.28–1.50 (m, 2H), 1.41 (s, 9H), 1.50–1.82 (m, 4H), 2.32 (s, 3H), 3.68–3.82 (m, 0.6H), 3.82–3.93 (m, 0.4H), 4.67–4.82 (m, 1.4H), 4.87–5.0 (m, 0.4H), 5.02–5.14 (m, 0.6H), 5.44 (d, J=6.8 Hz, 0.6H )

EXAMPLE 29

Preparation of
2-((2S)-2-tert-Butoxycarbonylamino-1-hydroxy-4-methylpentyl)-3-ethylcyclopropenone (Compound No. 219 in Table 2)

IR (neat, cm$^{-1}$): 3360, 1852, 1696, 1622 NMR (CDCl$_3$, δ): 0.90 (d, J=7.2 Hz, 3H), 0.94 (d, J=7.1 Hz, 3H), 1.28 (t, J=7.7 Hz, 3H), 1.42 (s, 9H), 1.40–1.58 (m, 2H), 1.60–1.78 (m, 1H), 2.63 (q, J=7.7 Hz, 2H), 3.70–3.85 (m, 1H), 4.60–4.75 (m, 1H), 4.75–4.90 (m, 1H), 5.0–5.18 (m, 1H)

EXAMPLE 30

Preparation of
2-((2S)-2-tert-Butoxycarbonylamino-1-hydroxyhexyl)-3-isopentylcyclopropenone (Compound No. 233 in Table 2)

IR (neat, cm$^{-1}$): 3320, 1842, 1707, 1683, 1620 NMR (CDCl$_3$, δ): 0.83–0.98 (m, 9H), 1.28–1.85 (m, 9H), 1.41 (s, 9H), 2.66 (q, J=7.2 Hz, 2H), 3.67–3.95 (m, 1H), 4.60–4.70 (m, 1H), 4.70–4.78 (m, 1H), 4.98–5.08 (m, 1H)

EXAMPLE 31

Preparation of 2-((1S, 2S ) -2-tert-Butoxycarbonylamino-1-hydroxyhexyl)-3-((Z)-1-hexenyl) cycloplopropenone (Compound No. 257 in Table 2)

IR (neat, cm$^{-1}$): 3270, 1842, 1710 , 1690, 1635 NMR (CDCl$_3$, δ): 0.80–0.97 (m, 6H), 1.25–1.83 (m, 10H), 1.40 (s, 9H), 2.59 (q, J=7.0 Hz, 2H), 3.75 (m, 1H), 4.70 (m, 1H), 4.79 (d, J=4.7 Hz, 1H), 5.01 (d, J=8.6 Hz, 1H), 6.26 (d, J=11 Hz, 1H), 6.40–6.55 (m, 1H)

EXAMPLE 32

Preparation of
2-((2S)-2-tert-Butoxycarbonylamino-1-hydroxyhexyl)-3-phenylcyclopropenone (Compound No. 285 in Table 2)

NMR (CDCl$_3$, δ): 0.86–0.97 (m, 3H), 1.28–1.51 (m, 4H), 1.31 (s, 1.8H), 1.34 (s, 7.2H), 1.52–1.93 (m, 2H), 3.73–3.88 (m, 0.8H), 3.93–4.03 (m, 0.2H), 4.84 (d, J=6.8 Hz, 0.2H), 4.91–5.03 (m, 1H), 5.12–5.27 (m, 1.6H), 5.73 (d, J=8.1 Hz, 0.2H), 7.42–7.60 (m, 3H), 7.95–8.05 (m, 2H)

EXAMPLE 33

Preparation of
2-((2S)-2-tert,Butoxycarbonylamino-1-hydroxyhexyl)-3-(2-tolyl) cyclopropenone (Compound No. 343 in Table 2 )

NMR (CDCl$_3$, δ): 0.85–0.96 (m, 3H), 1.28–1.51 (m, 13H), 1.53–1.95 (m, 2H), 2.68 (s, 3H), 3.72–3.88 (m, 0.7H), 3.94–4.05 (m, 0.3H), 4.75–5.18 (m, 2.7H), 5.59 (d,

J=8.1 Hz, 0.3H), 7.25–7.34 (m, 2H), 7.38–7.47 (m, 1H), 8.07–8.16 (m, 1H)

EXAMPLE 34

Preparation of 2((2S)-2-tert-Butoxycarbonylamino-1-hydroxyhexyl)-3-(5-trimethylsilyl-2-thienyl)cyclopropenone (Compound No. 411 in Table 2)

NHR (CDCl3, δ): 0.34 (s, 2.7H), 0.35 (s, 6.3H), 0.86–0.97 (m, 3H), 1.25–1.52 (m, 4H), 1.32 (s. 2.7H), 1.35 (s, 6.3H), 1.53–1.92 (m, 2H), 3.68–3.82 (m, 0.7H), 3.92–4.02 (m, 0.3H), 4.65–5.09 (m, 2.7H), 5.69 (d, J=7.7 Hz, 0.3H), 7.28 (d, J=4.1 Hz, 0.3H), 7.29 (d, J=4.1 Hz, 0.7H), 7.82 (d, J=4.1 Hz, 1H)

EXAMPLE 35

Preparation of 2((2S)-2-tert-Butoxycarbonylamino-1-hydroxy-3-methylbutyl)-3-(1-hydroxy-1-methylethyl)cyclopropenone (Compound No. 427 in Table 2)

IR (neat, cm⁻¹): 3430, 3300, 1840, 1683, 1628 NMR (CDCl3, δ): 0.98 (d, J=6.8 Hz, 1.8H), 1.04 (d, J=6.8 Hz, 1.8H), 1.05 (d, J=6.7 Hz, 1.2H), 1.10 (d, J=6.8 Hz, 1.2H), 1.41 (s, 5.4H), 1.43 (s, 3.6H), 1.48–1.57 (m, 6H), 1.90–2.12 (m, 1H), 3.65–3.80 (m, 1H), 4.20 (s, 0.4H), 4.76 (d, J=7.7 Hz, 0.4H), 4.85–4.17 (m, 2.8H), 5.59 (m, 0.4H)

EXAMPLE 36

Preparation of 2-((2S)-2-tert-Butoxycarbonylamino-1-hydroxy-3-methylbutyl)-3[(hydroxy)(phenyl)methyl]cyclopropenone (Compound No. 443 in Table 2)

IR (neat, cm⁻¹): 3440, 3330, 1845, 1716, 1683, 1630 NMR (CDCl3, δ): 0.96–1.11 (m, 6H), 1.18 (s, 1.9H), 1.37 (s, 1.0H), 1.39 (s, 3.6H), 1.43 (s, 2.5H), 1.90–2.15 (m, 1H), 3.68–3.78 (m, 0.3H), 3.78–3.89 (m, 0.7H), 4.89–5.40 (m, 1H), 5.16 (d, J=11 Hz, 0.7H), 5.40 (d, J=11 Hz, 0.3H), 5.30–5.41 (m, 1H), 5.62 (d, J=9.2 Hz, 0.3H), 5.80 (d, J=9.2 Hz, 0.7H), 5.86 (s, 1H), 7.50–7.86 (m, 3H), 7.86–8.11 (m, 2H)

EXAMPLE 37

Preparation of 2-((2S)-2-amino-1-hydroxyhexyl)cyclopropenone p-toluene sulfonate (Compound No. 179 in Table 2)

To 5 ml of a dichloroethane solution of 150 mg of 2-((2S)-2-tert-butoxycarbonylamino-1-hydroxyhexyl)cyclopropenone obtained in Example 22 was added 106 mg of p-toluene sulfonate monohydrate. After stirring at room temperature for 5 hours, the solvent was distilled off under reduced pressure to give 250 mg of the titled product.

NMR (CD3OD, δ): 0.93–1.10 (m, 3H), 1.30–1.65 (m, 4H), 1.65–2.05 (m, 2H), 2.41 (s, 3H), 3.40–3.60 (m, 0.7H), 3.60–3.75 (m, 0.3H), 4.89 (d, J=4 Hz, 0.7H), 5.15 (d, J=4 Hz, 0.3H), 7.28 (d, J=8 Hz, 2H), 7.74 (d, J=8 Hz, 2H), 9.12 (s, 0.7H), 9.18 (s, 0.3H)

EXAMPLE 38

Preparation of 2-((2S)-2-amino-1-hydroxy-3-methylbutyl)-3-phenylcyclopropenone hydrochloride (Compound No. 262 in Table 2)

To 8 ml of a dioxane solution of 3.12 g of 2-((2S)-2-tert-butoxycarbonylamino-1-hydroxy-3-methylbutyl)-3-phenylcyclopropenone 2,2-dimethyl, 1,3-propanediyl acetal obtained in Example 1 was added 24 ml of a dioxane solution containing 4 N HCl, and the mixture was stirred for 20 minutes. The resulting crystal was filtered and washed with dioxane, to give 1.87 g of the titled product.

Yield: 94% IR (KBr, cm⁻¹): 3200, 2975, 1855, 1618, 1510, 1450, 1055, 770, 690 NMR (CD3OD, δ): 1.21 (t, J=7 Hz, 4.5H), 1.24 (t, J=7 Hz, 1.5H), 2.0–2.2 (m, 0.25H), 2.2–2.4 (m, 0.75H), 3.38 (t, J=6 Hz, 0.25H), 3.45 (t, J=6 Hz, 0.75H), 5.21 (d, J=6 Hz, 0.75H), 5.45 (d, J=6 Hz, 0.25H), 7.60–7.80 (m, 3H), 8.10–8.20 (m, 2H)

In the same manner as in Examples 37 and 38, the following compounds were produced.

EXAMPLE 39

Preparation of 2-((1S, 2S)-2-amino-1-hydroxy-4-methylpentyl)cyclopropenone p-toluene sulfonate (Compound No. 173 in Table 2)

NMR (CD3OD, δ): 1.02 (d, J=6.2 Hz, 3H), 1.06 (d, J=6.3 Hz, 3H), 1.60–1.95 (m, 3H), 2.42 (s, 3H), 3.58 (m, 1H), 4.88 (d, J=4.9 Hz, 1H), 7.31 (d, J=8.2 Hz, 2H), 7.75 (d, J=8.2 Hz, 2H), 9.11 (s, 1H)

EXAMPLE 40

Preparation of 2-((2S)-2-amino-1-hydroxy-3-phenylpropyl)cyclopropenone p-toluene sulfonate (Compound No. 200 in Table 2)

NMR (CD3OD, δ): 2.41 (s, 3H), 3.03–3.30 (m, 2H), 3.80–4.10 (m, 1H), 4.75–5.00 (m, 1H), 7.15–7.45 (m, 7H), 7.75 (d, J=8.1 Hz, 2H), 8.88 (s, 0.3H), 9.04 (s, 0.7H)

EXAMPLE 41

Preparation of 2-((2S)-2-amino-1-hydroxy-4-methylpentyl)-3-ethylcyclopropenone p-toluene sulfonate (Compound No. 220 in Table 2)

NMR (CD3OD, δ): 0.95–1.15 (m, 6H), 1.55–1.95 (m, 3H), 2.41 (s, 3H), 2.68–2.88 (m, 2H), 3.40–3.60 (m, 1H), 4.75–4.85 (m, 1H), 7.27 (d, J=8.0 Hz, 2H), 7.75 (d, J=8.0 Hz, 2H)

EXAMPLE 42

Preparation of 2-((1S, 2S)-2-amino-1-hydroxyhexyl-3-((E)-1-hexenyl)cyclopropenone p-toluene sulfonate (Compound No. 252 in Table 2)

IR (KBr, cm⁻¹): 3422, 1845, 1630, 1601 NMR (CD3OD, δ): 0.80–1.05 (m, 6H), 1.20–1.95 (m, 10H), 2.36 (s, 3H), 2.32–2.40 (m, 2H), 3.25–3.45 (m, 1H), 4.82 (d, J=7.3 Hz, 1H), 6.38 (d, J=16 Hz, 1H), 7.02 (dd, J=16 Hz, 7.0 Hz, 1H), 7.24 (d, J=8.0 Hz, 2H), 7.70 (d, J=8.0 Hz, 2H)

EXAMPLE 43

Preparation of 2-((1S, 2S)-2-amino-1-hydroxyhexyl)-3-((Z)-1-hexenyl)cyclopropenone p-toluene sulfonate (Compound No. 258 in Table 2)

IR (neat, cm⁻¹): 3260, 1845, 1633 NMR (CDCl3, δ): 0.73 (t, J=7.1 Hz, 3H), 0.89 (t, J=6.7 Hz, 3H), 1.08–1.95 (m, 10H), 2.35 (s, 3H), 2.40–2.65 (m, 2H), 3.33 (m, 1H), 3.92 (s, 3H), 4.88 (m, 1H), 6.21 (d, J=10 Hz, 1H), 6.40

(dd, J=10 Hz, 6.8 Hz, 1H), 7.14 (d, J=6.7 Hz, 2H), 7.71 (d, J=6.7 Hz, 2H), 7.81 (m, 1H)

EXAMPLE 44

Preparation of 2-((2S)-1-hydroxy-3-methyl-2-methylaminobutyl)-3-phenylcyclopropenone hydrochloride (Compound No. 282 in Table 2)

IR (KBr, cm$^{-1}$): 3422, 1858, 1626 NMR (CD$_3$OD, δ: 0.78–0.95 (m, 6H), 2.05–2.40 (m, 1H), 2.79 (s, 3H), 3.47 (m, 1H), 5.28 (d, J=4.5 Hz, 0.5H), 5.43 (d, J=4.4 Hz, 0.5H), 7.55–7.75 (m, 3H), 7.95–8.13 (m, 2H)

EXAMPLE 45

Preparation of 2-(2-amino-1-hydroxy-2-methylpropyl)-3-phenylcyclopropenone hydrochloride (Compound No. 298 in Table 2)

IR (KBr, cm$^{-1}$): 3300, 3250, 1858, 1620 NMR (CD$_3$OD, δ): 1.42 (s, 3H), 1.57 (s, 3H), 4.98 (s, 1H), 7.55–7.78 (m, 3H), 8.07 (d, J=7.3 Hz, 2H)

EXAMPLE 46

Preparation of 2-((2S)-2-amino-1-hydroxy-3-methylbutyl)-3-(1-hydroxy-1-methylethyl) cyclopropenone hydrochloride (Compound No. 428 in Table 2)

IR (KBr, cm$^{-1}$): 3420, 1846, 1615 NMR (CD$_3$OD, δ: 1.09 (d, J=6.9 Hz, 2.1H), 1.13 (d, J=6.9 Hz, 2.1H), 1.14 (s, 1.8H), 1.56 (s, 4.2H), 1.58 (s, 1.8H), 1.99 (m, 0.3H), 2.15 (m, 0.7H), 3.25 (m, 0.3H), 3.39 (m, 0.7H), 5.01 (d, J=5.5 Hz, 0.7H), 5.19 (d, J=4.5 Hz, 0.3H)

EXAMPLE 47

Preparation of 2-((2S)-2-amino-1-hydroxy-3-methylbutyl)-(4-fluorophenyl) cyclopropenone (Compound No. 314 in Table 2)

IR (KBr, cm$^{-1}$): 3280, 1858, 1620, 1600 NMR (CD$_3$OD, δ): 1.05–1.33 (m, 6H), 2.07 (m, 0.2H), 2.29 (m, 0.8H), 3.38 (m, 0.2H), 3.44 (m, 0.8H), 5.20 (d, J=6.1 Hz, 0.8H), 5.41 (d, J=4.7 Hz, 0.2H), 7.38–7.52 2H), 8.15–8.32 (m, 2H)

EXAMPLE 48

Preparation of 2-((2S)-2-amino-1-hydroxy-3-methylbutyl)-3-[(hydroxy)(phenyl)methyl]cyclopropenone hydrochlorine (Compound No. 444 in Table 2)

IR (KBr, cm$^{-1}$): 3430, 1846, 1626 NMR (CD$_3$OD, δ): 1.0–1.20 (m, 6H), 1.90–2.22 (m, 1H), 3.20–3.45 (m, 1H), 5.0–5.25 (m, 1H), 5.97 (s, 0.75H), 6.0 (s, 0.25H), 7.28–7.45 (m, 3H), 7.45–7.60 (m, 2H)

EXAMPLE 49

Preparation of 2-((2S)-2-methoxycarbonylamino-3-methyl-1-hydroxybutyl)-3-phenylcyclopropenone (Compound No. 278 in Table 2)

IR (neat, cm$^{-1}$): 3333, 1856, 1705, 1622 NMR (CDCl$_3$, δ): 0.95–1.15 (m, 6H), 1.95–2.40 (m, 1H), 3.56 (s, 2.4H), 3.63 (s, 0.6H), 3.72 (m, 0.2H), 3.80 (m, 0.8H), 5.09 (d, J=4.5 Hz, 1H), 5.72 (d, J=6.7 Hz, 1H), 7.45–7.60 (m, 3H), 7.93–8.08 (m, 2H)

What we claim is:

1. Cyclopropene derivatives represented by formula (I):

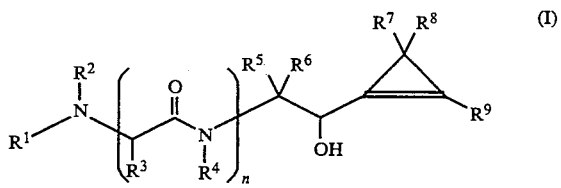

wherein:

$R^1$ represents hydrogen atom or a protective group for an amino group; $R^2$ represents hydrogen atom, a protective group for an amino group or a $C_1$–$C_5$ alkyl group;

$R^4$ and $R^6$ independently represent a hydrogen atom or $C_1$–$C_5$ alkyl group;

$R^3$ and $R^5$ independently represent a hydrogen atom or $C_1$–$C_{15}$ alkyl group optionally substituted with $C_3$–$C_{10}$ cycloalkyl group or $C_6$–$C_{10}$ aryl group; or when $R^5$ and $R^6$ are taken together, they represent a $C_2$–$C_6$ alkylene group;

$R^7$ and $R^8$ represent —$OR^{10}$ and —$OR^{11}$, respectively, wherein $R^{10}$ and $R^{11}$ independently represent $C_1$–$C_5$ alkyl group optionally substituted with phenyl group; or when $R^{10}$ and $R^{11}$ are taken together, they represent a $C_2$–$C_6$ alkylene group optionally substituted with one or more $C_1C_5$ alkyl groups; or when $R^7$ and $R^8$ are taken together, they represent =O;

$R^9$ represents a hydrogen atom, $C_1$–$C_{15}$ alkyl group, $C_3$–$C_{10}$ cycloalkyl group, $C_2$–$C_{15}$ alkenyl group, $C_6$–$C_{10}$ aryl group optionally substituted with one or more substituents selected from the group consisting of halogen atom, $C_1$–$C_5$ alkyl group, hydroxyl group and $C_1$–$C_5$ alkoxy group, heterocyclic selected from the group consisting of thienyl and furyl, optionally substituted with one or more substituents selected from the group consisting of $C_3$–$C_{12}$ trialkylsilyl group, halogen atom, $C_1$–$C_5$ alkyl group, hydroxyl group and $C_1$–$C_5$ alkoxy group, or —$CR^{12}R^{13}OH$ wherein $R^{12}$ and $R^{13}$ independently represent a hydrogen atom, $C_1$–$C_5$ alkyl group or $C_6$–$C_{10}$ aryl group; or when $R^{12}$ and $R^{13}$ are taken together they represent a $C_3$–$C_{10}$ cycloalkyl group; and n represents 0.

2. Compounds according to claim 1, wherein $R^1$ represents hydrogen atom, tert-butoxycarbonyl group, benzyloxycarbonyl group, methoxycarbonyl group, 9-fluorenylmethoxycarbonyl group, p-toluene sulfonyl group, or trityl group; $R^2$, $R^4$ and $R^6$ independently represent hydrogen atom or $C_1$–$C_3$ alkyl group; $R^3$ and $R^5$ independently represent hydrogen atom or $C_1$–$C_5$ alkyl group optionally substituted with $C_3$–$C_8$ cycloalkyl group, phenyl group or naphthyl group; or $R^5$, when taken together with $R^6$ represents $C_2$–$C_5$ alkylene group; $R^7$ and $R^8$ represent —$OR^{10}$ and —$OR^{11}$, respectively, wherein, $R^{10}$ and $R^{11}$ independently represent $C_1$–$C_3$ alkyl group optionally substituted with phenyl group; or $R^{10}$ when taken together with $R^{11}$ represents $C_2$–$C_4$ alkylene group optionally substituted with one or more $C_1$–$C_3$ alkyl groups; or $R^7$, when taken together with $R^8$ represents =O; $R^9$ represents hydrogen atom; $C_1$–$C_6$ alkyl group; $C_3$–$C_8$ cycloalkyl group; $C_2$–$C_8$ alkenyl group; phenyl group or naphthyl group each optionally substituted with one or more substituents selected from the group consisting of halogen atom, $C_1$–$C_5$ alkyl group and $C_1$–$C_5$ alkoxy group; heterocyclic selected from the group consisting of thienyl and furyl, optionally substituted with one or more substituents selected from the group consisting of halogen atom, $C_1$–$C_5$ alkyl group, $C_1$–$C_5$ alkoxy group, and $C_3$–$C_{12}$ trialkylsilyl group; or —$CR^{12}R^{13}OH$ wherein $R^{12}$ and $R^{13}$ independently represent hydrogen atom, $C_1$–$C_3$ alkyl group or phenyl group.

3. Compounds according to claim 1, wherein $R^1$ represents hydrogen atom, tert-butoxycarbonyl group, benzyloxycarbonyl group or methoxycarbonyl group; $R^2$, $R^4$ and $R^6$ independently represent hydrogen atom or $C_1$–$C_3$ alkyl group; $R^3$ and $R^5$ independently represent hydrogen atom or $C_1$–$C_5$ alkyl group optionally substituted with phenyl group; $R^7$ and $R^8$ represent —$OR^{10}$ and —$OR^{11}$, respectively, wherein $R^{10}$, when taken together with $R^{11}$ represents $C_2$–$C_4$ alkylene group optionally substituted with one or more $C_1$–$C_3$ alkyl groups; or $R^7$, when taken together with $R^8$ represents =O; $R^9$ represents hydrogen atom; $C_1$–$C_6$ alkyl group; $C_2$–$C_8$ alkenyl group; phenyl group optionally substituted with one or more substituents selected from the group consisting of halogen atom and $C_1$–$C_5$ alkyl group; furyl group or thienyl group each optionally substituted with one or more $C_3$–$C_{12}$ trialkylsilyl groups; or —$CR^{12}R^{13}OH$ wherein $R^{12}$ and $R^{13}$ independently represent hydrogen atom, $C_1$–$C_3$ alkyl group or phenyl group.

* * * * *